US011219680B2

(12) United States Patent
MacNair et al.

(10) Patent No.: US 11,219,680 B2
(45) Date of Patent: Jan. 11, 2022

(54) POLYSACCHARIDE-PROTEIN CONJUGATES UTILIZING DIPHTHERIA TOXIN FRAGMENT B AS A CARRIER

(71) Applicants: Merck Sharp & Dohme Corp., Rahway, NJ (US); John E. MacNair, Lansdale, PA (US); Michael A. Winters, Doylestown, PA (US); Thomas Svab, Plains, PA (US); Sheng-Ching Wang, Eagleville, PA (US); William J. Smith, Harleysville, PA (US); Cecilia Giovarelli, Allentown, PA (US)

(72) Inventors: John E. MacNair, Lansdale, PA (US); Michael A. Winters, Doylestown, PA (US); Thomas Svab, Plains, PA (US); Sheng-Ching Wang, Eagleville, PA (US); William J. Smith, Harleysville, PA (US); Cecilia Giovarelli, Allentown, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/487,621

(22) PCT Filed: Feb. 20, 2018

(86) PCT No.: PCT/US2018/018656
§ 371 (c)(1),
(2) Date: Aug. 21, 2019

(87) PCT Pub. No.: WO2018/156465
PCT Pub. Date: Aug. 30, 2018

(65) Prior Publication Data

US 2020/0061179 A1 Feb. 27, 2020

Related U.S. Application Data

(60) Provisional application No. 62/463,225, filed on Feb. 24, 2017.

(51) Int. Cl.

| | |
|---|---|
| *A61K 39/09* | (2006.01) |
| *A61K 47/64* | (2017.01) |
| *C07K 14/34* | (2006.01) |
| *A61K 38/00* | (2006.01) |
| *A61K 39/00* | (2006.01) |

(52) U.S. Cl.
CPC .......... *A61K 39/092* (2013.01); *A61K 47/646* (2017.08); *A61K 47/6415* (2017.08); *C07K 14/34* (2013.01); *A61K 38/00* (2013.01); *A61K 2039/6037* (2013.01)

(58) Field of Classification Search
None
See application file for complete search history.

(56) References Cited

U.S. PATENT DOCUMENTS

| | | | | |
|---|---|---|---|---|
| 4,033,819 | A | 7/1977 | Helting et al. | |
| 5,827,934 | A | 10/1998 | Villemez et al. | |
| 5,843,711 | A * | 12/1998 | Collier | C07K 14/34 435/69.1 |
| 8,192,746 | B2 * | 6/2012 | Caulfield | A61P 37/00 424/197.11 |
| 2014/0242635 | A1 | 8/2014 | Dehottay et al. | |
| 2016/0009768 | A1 | 1/2016 | Davis et al. | |

FOREIGN PATENT DOCUMENTS

| | | | |
|---|---|---|---|
| WO | WO199700697 | | 1/1997 |
| WO | WO2012078482 | A1 | 6/2012 |
| WO | WO2014095771 | A1 | 6/2014 |

* cited by examiner

*Primary Examiner* — Brian Gangle
(74) *Attorney, Agent, or Firm* — Matthew A. Left; Alysia A. Finnegan

(57) ABSTRACT

The present invention provides immunogenic compositions having one or more polysaccharide-protein conjugates in which polysaccharides obtained from bacterial capsules are conjugated to diphtheria toxin fragment B (DTFB) or a variant thereof. The immunogenic compositions may be multivalent pneumococcal polysaccharide conjugate compositions in which polysaccharides from one or more *Steptococcus pneumoniae* serotypes are conjugated to diphtheria toxin fragment B (DTFB) and, optionally, additional polysaccharides from one or more different *Steptococcus pneumoniae* serotypes are conjugated to one or more other carrier proteins.

10 Claims, 20 Drawing Sheets

POLYSACCHARIDE-PROTEIN CONJUGATES UTILIZING DIPHTHERIA TOXIN FRAGMENT B AS A CARRIER

FIELD OF INVENTION

The present invention provides immunogenic compositions having one or more polysaccharide-protein conjugates in which at least one polysaccharide obtained from encapsulated bacteria, e.g., *Steptococcus pneumoniae*, is conjugated to diphtheria toxin fragment B (DTFB) or a variant thereof.

BACKGROUND OF THE INVENTION

*Streptococcus pneumoniae*, one example of an encapsulated bacterium, is a significant cause of serious disease world-wide. In 1997, the Centers for Disease Control and Prevention (CDC) estimated there were 3,000 cases of pneumococcal meningitis, 50,000 cases of pneumococcal bacteremia, 7,000,000 cases of pneumococcal otitis media and 500,000 cases of pneumococcal pneumonia annually in the United States. See Centers for Disease Control and Prevention, MMWR Morb Mortal Wkly Rep 1997, 46(RR-8):1-13. Furthermore, the complications of these diseases can be significant with some studies reporting up to 8% mortality and 25% neurologic sequelae with pneumococcal meningitis. See Arditi et al., 1998, Pediatrics 102:1087-97.

The multivalent pneumococcal polysaccharide vaccines that have been licensed for many years have proved invaluable in preventing pneumococcal disease in adults, particularly, the elderly and those at high-risk. However, infants and young children respond poorly to unconjugated pneumococcal polysaccharides. Bacterial polysaccharides are T-cell-independent immunogens, eliciting weak or no response in infants. Chemical conjugation of a bacterial polysaccharide immunogen to a carrier protein converts the immune response to a T-cell-dependent one in infants. Diphtheria toxoid (DTx, a chemically detoxified version of DT) and $CRM_{197}$ have been described as carrier proteins for bacterial polysaccharide immunogens due to the presence of T-cell-stimulating epitopes in their amino acid sequences.

The pneumococcal conjugate vaccine, Prevnar®, containing the 7 most frequently isolated serotypes (4, 6B, 9V, 14, 18C, 19F and 23F) causing invasive pneumococcal disease in young children and infants at the time, was first licensed in the United States in February 2000. Following universal use of Prevnar® in the United States, there has been a significant reduction in invasive pneumococcal disease in children due to the serotypes present in Prevnar®. See Centers for Disease Control and Prevention, MMWR Morb Mortal Wkly Rep 2005, 54(36):893-7. However, there are limitations in serotype coverage with Prevnar® in certain regions of the world and some evidence of certain emerging serotypes in the United States (for example, 19A and others). See O'Brien et al., 2004, Am J Epidemiol 159:634-44; Whitney et al., 2003, N Engl J Med 348:1737-46; Kyaw et al., 2006, N Engl J Med 354:1455-63; Hicks et al., 2007, J Infect Dis 196:1346-54; Traore et al., 2009, Clin Infect Dis 48:S181-S189.

Prevnar 13® is a 13-valent pneumococcal polysaccharide-protein conjugate vaccine including serotypes 1, 3, 4, 5, 6A, 6B, 7F, 9V, 14, 18C, 19A, 19F and 23F. See, e.g., U.S. Patent Application Publication No. US 2006/0228380 A1, Prymula et al., 2006, Lancet 367:740-48 and Kieninger et al., Safety and Immunologic Non-inferiority of 13-valent Pneumococcal Conjugate Vaccine Compared to 7-valent Pneumococcal Conjugate Vaccine Given as a 4-Dose Series in Healthy Infants and Toddlers, presented at the 48th Annual ICAAC/ISDA 46th Annual Meeting, Washington D.C., Oct. 25-28, 2008. See, also, Dagan et al., 1998, Infect Immun. 66: 2093-2098 and Fattom, 1999, Vaccine 17:126.

Chinese Patent Application Publication No. CN 101590224 A describes a 14-valent pneumococcal polysaccharide-protein conjugate vaccine including serotypes 1, 2, 4, 5, 6A, 6B, 7F, 9N, 9V, 14, 18C, 19A, 19F and 23F.

U.S. Pat. No. 8,192,746 describes a 15-valent pneumococcal polysaccharide-protein conjugate vaccine having serotypes 1, 3, 4, 5, 6A, 6B, 7F, 9V, 14, 18C, 19A, 19F, 22F, 23F and 33F, all individually conjugated to $CRM_{197}$ polypeptides.

Multiple carrier protein systems have also been described. See e.g., U.S. Patent Application Publication Nos. 20100209450, 20100074922, 20090017059, 20090010959 and 20090017072.

Formulations comprising *S. pneumoniae* polysaccharide-protein conjugates and surfactants including polysorbate 80 (PS-80) and poloxamer 188 (P188) have been disclosed. See U.S. Pat. No. 8,562,999 and U.S. Patent Application Publication No. US20130273098, respectively.

SUMMARY OF THE INVENTION

The present invention provides for the use of Diphtheria Toxin Fragment B (DTFB) as a carrier protein. The present invention provides an immunogenic composition comprising a polysaccharide-protein conjugate wherein the protein is diphtheria toxin fragment B (DTFB) or a variant thereof. In certain embodiments, the polysaccharide is a capsular polysaccharide from *Haemophilus influenza* type B, *Klebsiella pneumoniae* K1, *Neisseria meningitides*, *Streptococcus pneumoniae*, or *Salmonella typhi*. In certain aspects, the immunogenic composition comprises a multivalent composition comprising more than one polysaccharide-protein conjugate from different organisms or different serotypes from the same organism. In certain aspects, the polysaccharides are capsular polysaccharides from *Streptococcus pneumoniae*. In one aspect, the capsular polysaccharides are from at least one of serotypes 1, 2, 3, 4, 5, 6A, 6B, 6C, 6D, 7B, 7C, 7F, 8, 9N, 9V, 10A, 11A, 12F, 14, 15A, 15B, 15C, 16F, 17F, 18C, 19A, 19F, 20, 21, 22A, 22F, 23A, 23B, 23F, 24F, 27, 28A, 31, 33F, 34, 35A, 35B, 35F, and 38 of *Streptococcus pneumoniae* conjugated to a first carrier protein selected from diphtheria toxin fragment B (DTFB) or a variant thereof. In one aspect, the carrier protein is DTFB or DTFB C8 (DT/$CRM_{197}$ C201).

In a specific embodiment, the immunogenic composition comprises serotype 3 capsular polysaccharide of *S. pneumoniae* conjugated to DTFB. The immunogenic composition may further comprise capsular polysaccharides from at least one additional serotype conjugated to a second carrier protein. The additional serotypes may be selected from one or more of serotypes 1, 2, 4, 5, 6A, 6B, 6C, 6D, 7B, 7C, 7F, 8, 9N, 9V, 10A, 11A, 12F, 14, 15A, 15B, 15C, 16F, 17F, 18C, 19A, 19F, 20, 21, 22A, 22F, 23A, 23B, 23F, 24F, 27, 28A, 31, 33F, 34, 35A, 35B, 35F, and 38 conjugated to a second carrier protein. The second carrier is optionally $CRM_{197}$. In certain embodiments, the additional serotypes can include each of serotypes 1, 4, 5, 6A, 6B, 7F, 9V, 14, 18C, 19A, 19F, 22F, 23F, and 33F conjugated to $CRM_{197}$.

In any of the embodiments or aspects of the invention, the immunogenic composition may further comprise an adjuvant. The adjuvant can be an aluminum-based adjuvant, optionally selected from the group consisting of aluminum phosphate, aluminum sulfate and aluminum hydroxide. In one aspect, the adjuvant is aluminum phosphate.

In a specific aspect, the immunogenic composition administered is a single 0.5 mL dose formulated to contain: 2 μg of each saccharide, except for 6B at 4 μg; about 32 μg $CRM_{197}$ carrier protein; about 2 μg of DTFB, 0.25 mg aluminum phosphate adjuvant; 150 mM sodium chloride (NaCl), 0.2% weight/volume (w/v) polysorbate 20 (PS-20), and 20 mM L-histidine buffer.

The present invention also relates to methods of inducing an immune response to a Streptococcus pneumoniae capsular polysaccharide, comprising administering to a human an immunologically effective amount of the immunogenic compositions directed to S. pneumoniae polysaccharides. In one aspect, the immunogenic composition administered is a single 0.5 mL dose formulated to contain: 2 μg of each saccharide, except for 6B at 4 μg; about 32 μg $CRM_{197}$ carrier protein; about 2 μg of DTFB, 0.25 mg aluminum phosphate adjuvant (APA); 150 mM sodium chloride and 20 mM L-histidine buffer.

The present invention also provides a formulation comprising (i) one or more polysaccharide-protein conjugates; (ii) a pH buffered saline solution having a pH in the range from 5.0 to 7.5; (ii) an aluminum salt; and (iv) a surfactant system selected from a) polysorbate 20 (PS-20) and (b) a poloxamer having a molecular weight in the range from 1100 Da to 17,400 Da and a polyol selected from propylene glycol (PG) and polyethylene glycol (PEG) 400. In certain embodiments, the surfactant system comprises a poloxamer which has a molecular weight in the range from 1100 Da to 17,400 Da, 7,500 Da to 15,000 Da, or 7,500 to 10,000 Da. The poloxamer can be poloxamer 188 or poloxamer 407. In certain aspects, final concentration of the poloxamer is from 0.001% to 5% w/v, from 0.025% to 1% w/v. In a specific aspect, the polyol is propylene glycol and is at final concentration from 1% to 20% w/v. In another specific aspect, the polyol is polyethylene glycol 400 and is at final concentration from 1% to 20% w/v.

In certain embodiments, the surfactant system comprises polysorbate 20. In certain aspects, the final concentration of the polysorbate 20 is in the range from 0.001% to 10% w/v, or from 0.025% to 2.5% w/v, or from 0.025% to 0.1% w/v. In certain aspects where the surfactant system comprises P188, the formulation further comprises a polyol selected from propylene glycol and polyethylene glycol. The polyethylene glycol or propylene glycol may be at a final concentration of 6% to 20% w/v. In certain embodiments, the polyethylene glycol is polyethylene glycol 400.

In certain embodiments, the pH buffered saline solution can have a pH in the range from 5.0 to 7.0. The buffer can be selected from the group consisting of phosphate, succinate, L-histidine, MES, MOPS, HEPES, acetate or citrate. In one aspect, the buffer is L-histidine at a final concentration of 5 mM to 50 mM, or succinate at a final concentration of 1 mM to 10 mM. In a specific aspect, the L-histidine is at a final concentration of 20 mM±2 mM. The salt in the pH buffered saline solution can be magnesium chloride, potassium chloride, sodium chloride or a combination thereof. In one aspect, the pH buffered saline solution is sodium chloride. The saline can be present at a concentration from 20 mM to 170 mM.

In certain embodiments, the polysaccharide-protein conjugates comprise one or more pneumococcal polysaccharides conjugated to a carrier protein. In certain aspects, the carrier protein is selected from $CRM_{197}$, diphtheria toxin fragment B (DTFB), DTFB C8, Diphtheria toxoid (DT), tetanus toxoid (TT), fragment C of TT, pertussis toxoid, cholera toxoid, E. coli LT, E. coli ST, exotoxin A from Pseudomonas aeruginosa, and combinations thereof. In one specific aspect, one or more of the polysaccharide-protein conjugates are conjugated to DTFB. In certain aspects, all of the polysaccharide-protein conjugates are prepared using reductive amination chemistry in an aqueous solvent. In this aspect, the polysaccharide-protein conjugate formulation can be a 15-valent pneumococcal conjugate formulation consisting essentially of S. pneumoniae polysaccharide from serotypes 1, 4, 5, 6A, 6B, 7F, 9V, 14, 18C, 19A, 19F, 22F, 23F and 33F conjugated to a $CRM_{197}$ polypeptide, and a S. pneumoniae polysaccharide from serotype 3 conjugated to a DTFB. In certain aspects, one or more of the polysaccharide protein conjugates is prepared using reductive amination in the non-aqueous solvent dimethysufloxide (DMSO). In this aspect, polysaccharide protein conjugates from serotypes 6A, 6B, 7F, 18C, 19A, 19F, and 23F can be prepared using reductive amination in DMSO, and polysaccharide protein conjugates from serotypes 1, 3, 4, 5, 9V, 14, 22F, and 33F can be prepared using reductive amination in aqueous solution.

The present invention also provides a method of making DTFB, the method comprising the steps of: a) digesting DT or $CRM_{197}$ with trypsin, b) adding DTT to reduce the disulfide bond between the A and B fragments. In certain embodiments, the DTT is at a concentration of at least 1 mM or the DTT is at a concentration of at least 5 mM.

The present invention also provides methods of purification of DTFB, comprising the steps of: a) applying a mixture comprising DTFB onto a multimodal ion exchange chromatography column in the presence of an equilibration buffer; and b) eluting DTFB from the column with an elution buffer. In certain embodiments, the elution buffer comprises at least 300 mM Tris and at least 1000 mM NaCl.

Figure 1A:
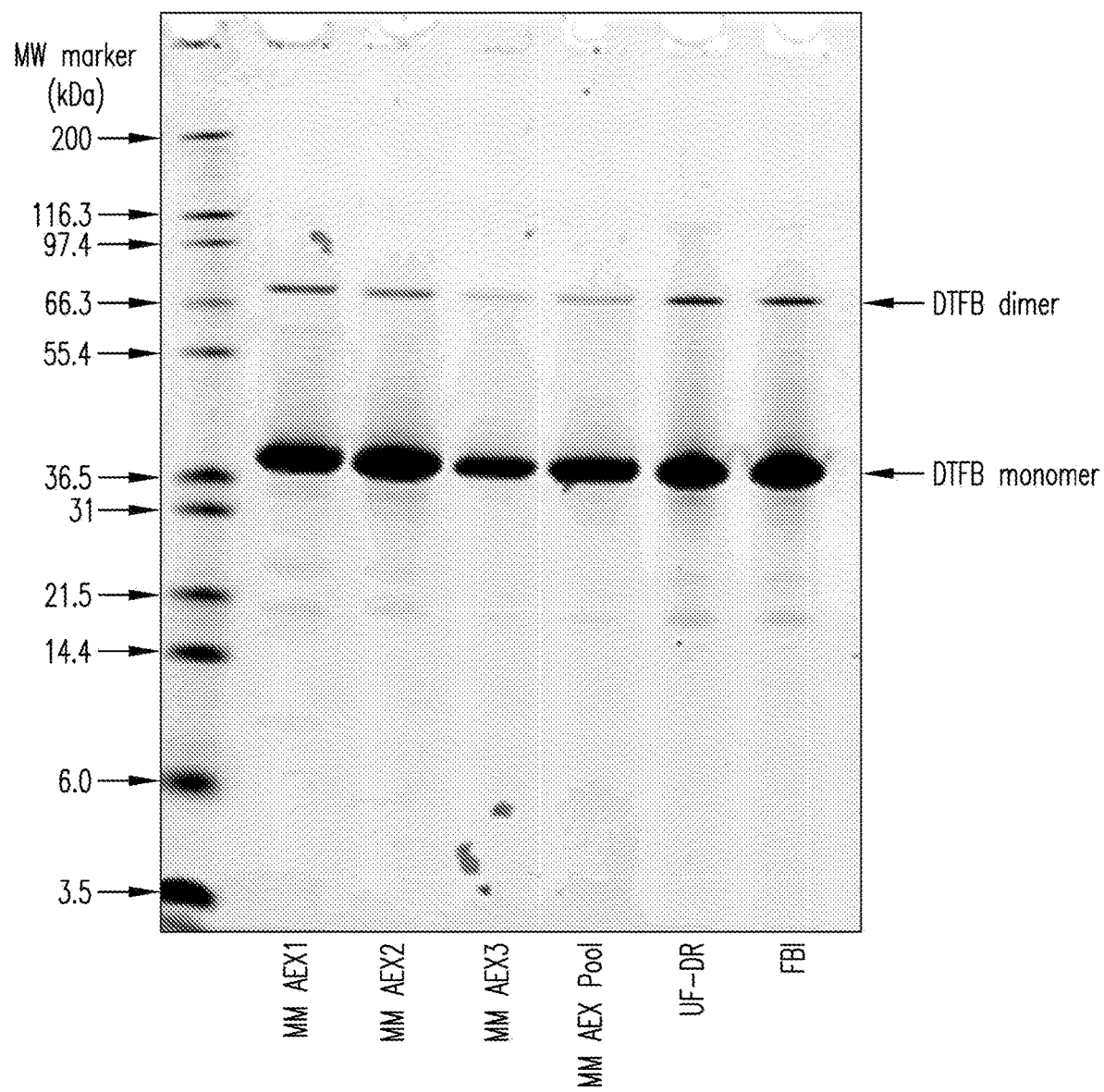
FIGS. 1A-D: SDS-PAGE analysis of DTFB process intermediates under non-reducing conditions. A: Samples shown are: Molecular weight standards (lane 1 from left); eluent product from three replicate multimodal anion exchange chromatography runs (MM AEX1, MM AEX2, MM AEX3, lanes 2-4); pooled eluent product from multimodal anion exchange chromatography runs (MM AEX Pool, lane 5); diafiltered retentate (UF-DR, lane 6); and final bulk intermediate after 0.2-micron filtration (FBI, lane 7). SDS PAGE: NuPAGE 4-12% Bis-Tris gel; 5 μg/lane; SYPRO Ruby protein gel stain.

B: SDS-PAGE analysis (NuPAGE 4-12% Bis-Tris gel; lanes 2, 4, 8, 10: 5 μg/lane; lane 6: 2 μg/lane; SYPRO Ruby protein gel stain) of DTFB process intermediates run under reducing conditions. Samples shown are: Mark-12 standards (lanes 1 and 12); purified $CRM_{197}$ used to generate DTFB ($CRM_{197}$, lanes 2 and 10); proteolytically-cleaved $CRM_{197}$ following trypsin digestion step, loaded onto multimodal cation exchange chromatography resin (MM CEX feed, lane 4); product from multimodal cation exchange chromatography (MM CEX product, lane 6); and final bulk intermediate after 0.2-micron filtration (DTFB-FBI, lane 8).

C: Samples shown are: molecular weight markers (lane 1 from left); initial concentrated retentate following multimodal cation exchange chromatography (ICR, lane 2); diafiltered retentate (UF-DR, lane 3); concentrated retentate after diafiltration (UF-OCR, lane 4); membrane flush for product recovery (UF-W, lane 5); final pooled retentate plus flush (UF-FR, lane 6); and final bulk intermediate after 0.2-micron filtration (FBI, lane 6). SDS-PAGE: 14% Tris-Glycine gel; 8.3-8.4 μg/lane; GelCode Blue protein gel stain.

D: SDS-PAGE analysis (NuPAGE 4-12% Bis-Tris gel; SYPRO Ruby protein gel stain) of DTFB process intermediates run under reducing conditions. Samples shown are: Mark-12 standards (lanes 1 and 12); proteolytically-cleaved $CRM_{197}$ following trypsin digestion step, loaded onto multimodal cation exchange chromatography resin (MM CEX feed, lane 2); purified $CRM_{197}$ used to generate DTFB ($CRM_{197}$, lane 3); flow-through during column loading (MM CEX flow-through, lane 4); wash of column after loading (MM CEX wash, lane 5); product collected after step elution from multimodal cation exchange chromatography (MM CEX product, lane 7; 10-fold diluted MM CEX product, lane 9); and late eluting product collected after step elution from multimodal cation exchange chromatography (Late eluting MM CEX product, lane 11).

Figure 2:
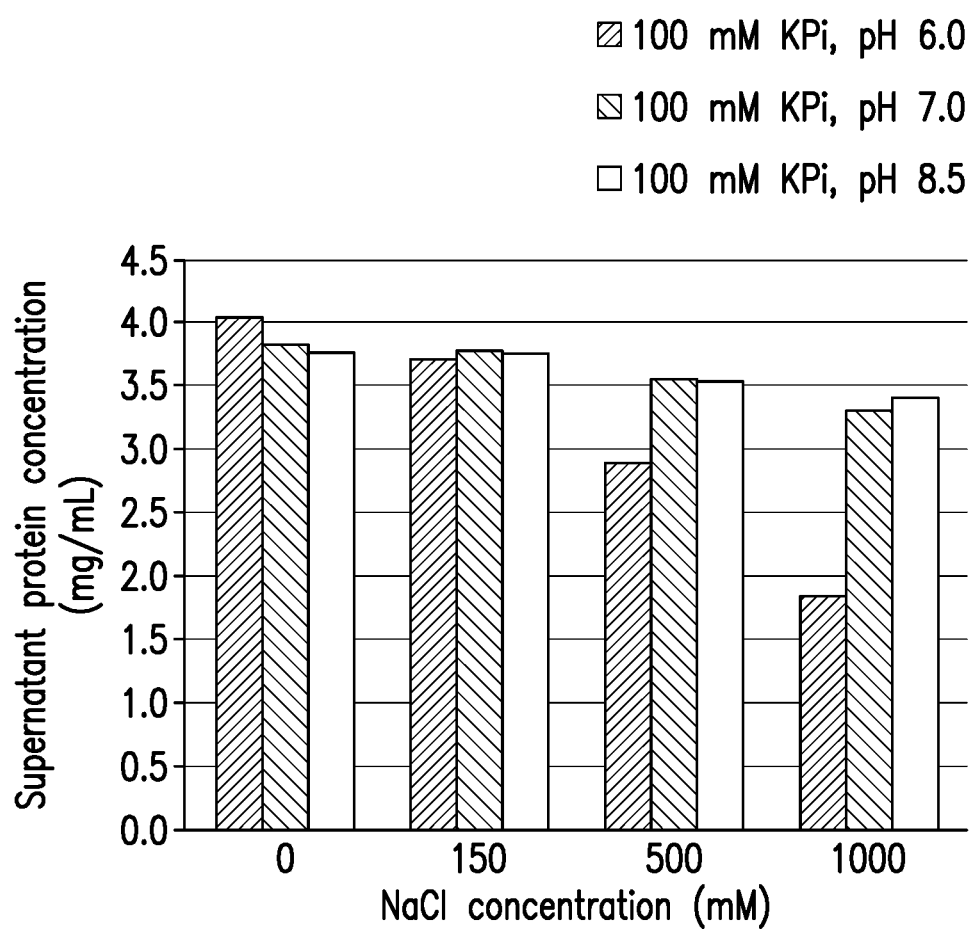

FIG. 2: DTFB protein concentration in 100 mM potassium phosphate (KPi) as a function of pH and sodium chloride (NaCl) concentration. Solutions were held overnight at room temperature and then centrifuged. Supernatants assayed by size exclusion chromatography with UV280 absorbance detection.

Figure 3:
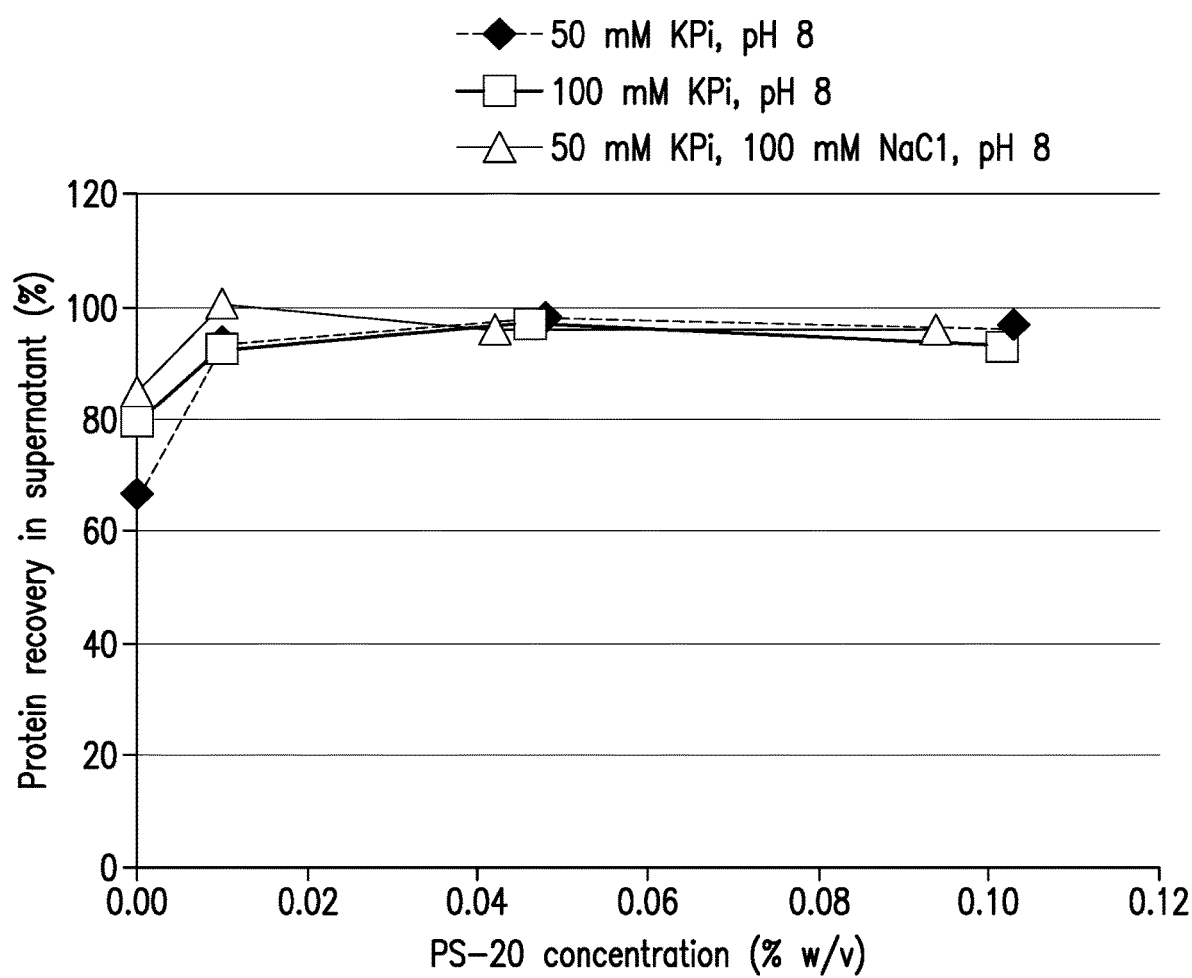

FIG. 3: DTFB protein concentration in potassium phosphate (KPi) solutions as a function of polysorbate 20 (PS-20) concentration. Solutions vortexed for 5 minutes at room temperature and then centrifuged. Supernatants assayed by size exclusion chromatography with UV280 absorbance detection.

Figure 4:
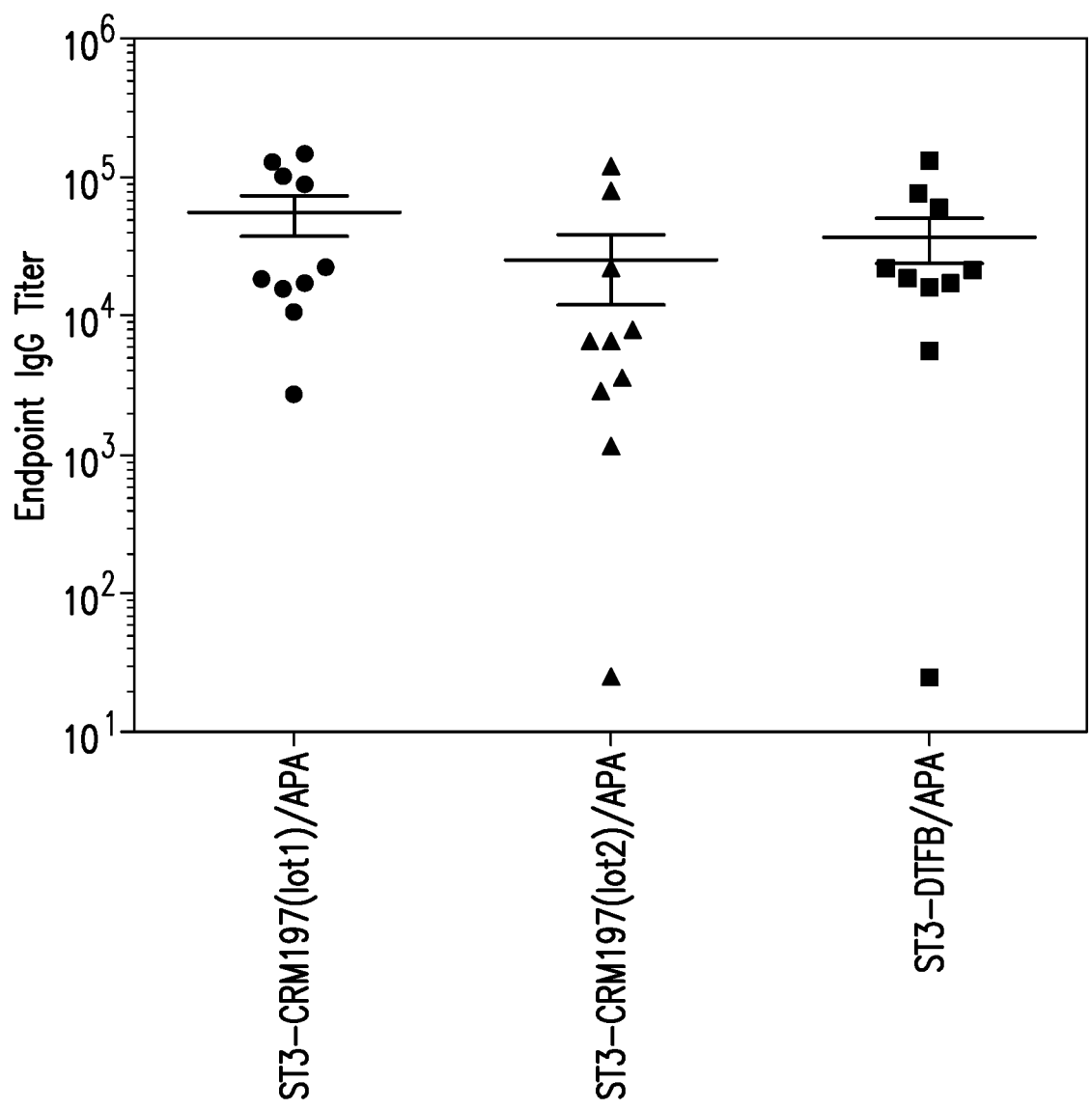

FIG. 4: ELISA antibody titers for mice immunized with *S. pneumoniae* serotype 3 polysaccharide conjugated to either $CRM_{197}$ or DTFB carrier protein and formulated with aluminum phosphate adjuvant (APA). Mice were immunized with one of two independent serotype 3-$CRM_{197}$ conjugate lots (lots 1 and 2).

Figure 5:
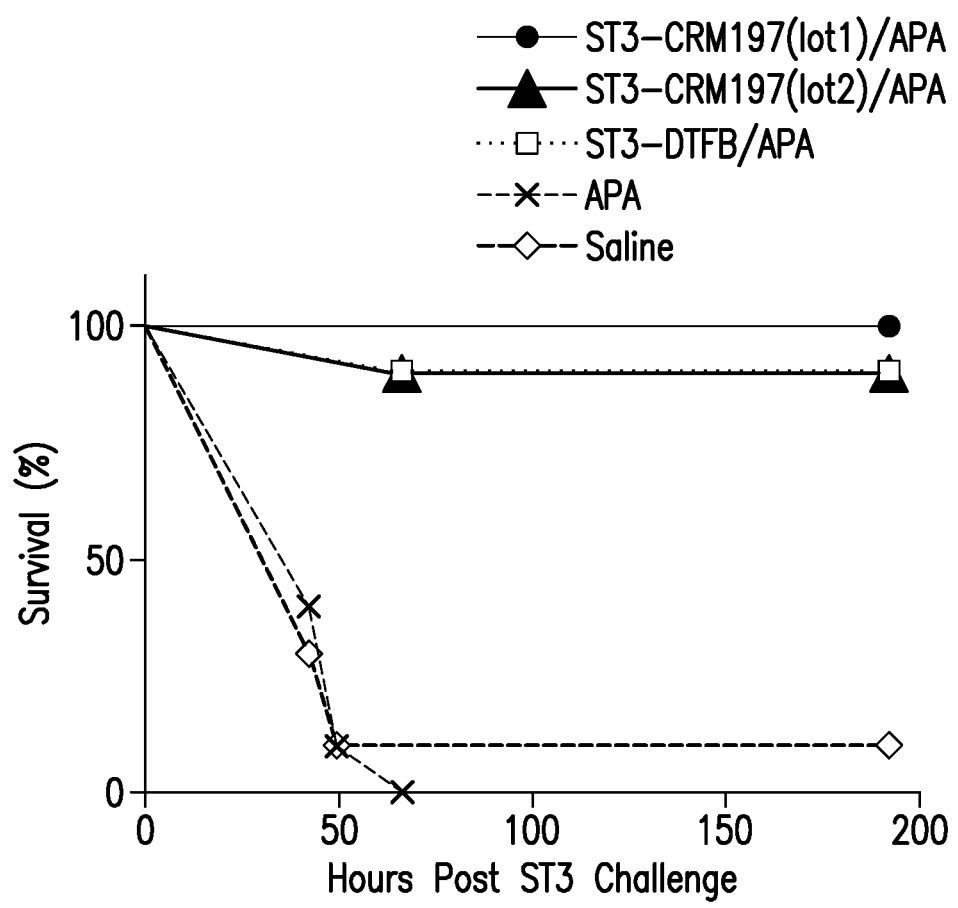

FIG. 5: Survival curves for mice immunized with *S. pneumoniae* serotype 3 capsular polysaccharide conjugated to either $CRM_{197}$ or DTFB carrier protein and formulated with aluminum phosphate adjuvant (APA). Mice were immunized with one of two independent serotype 3-$CRM_{197}$ conjugate lots (lots 1 and 2). Formulations of APA or saline only were also included in the study as controls. Following immunization, mice were subsequently intraperitoneally challenged with Serotype 3 bacteria.

Figure 6:
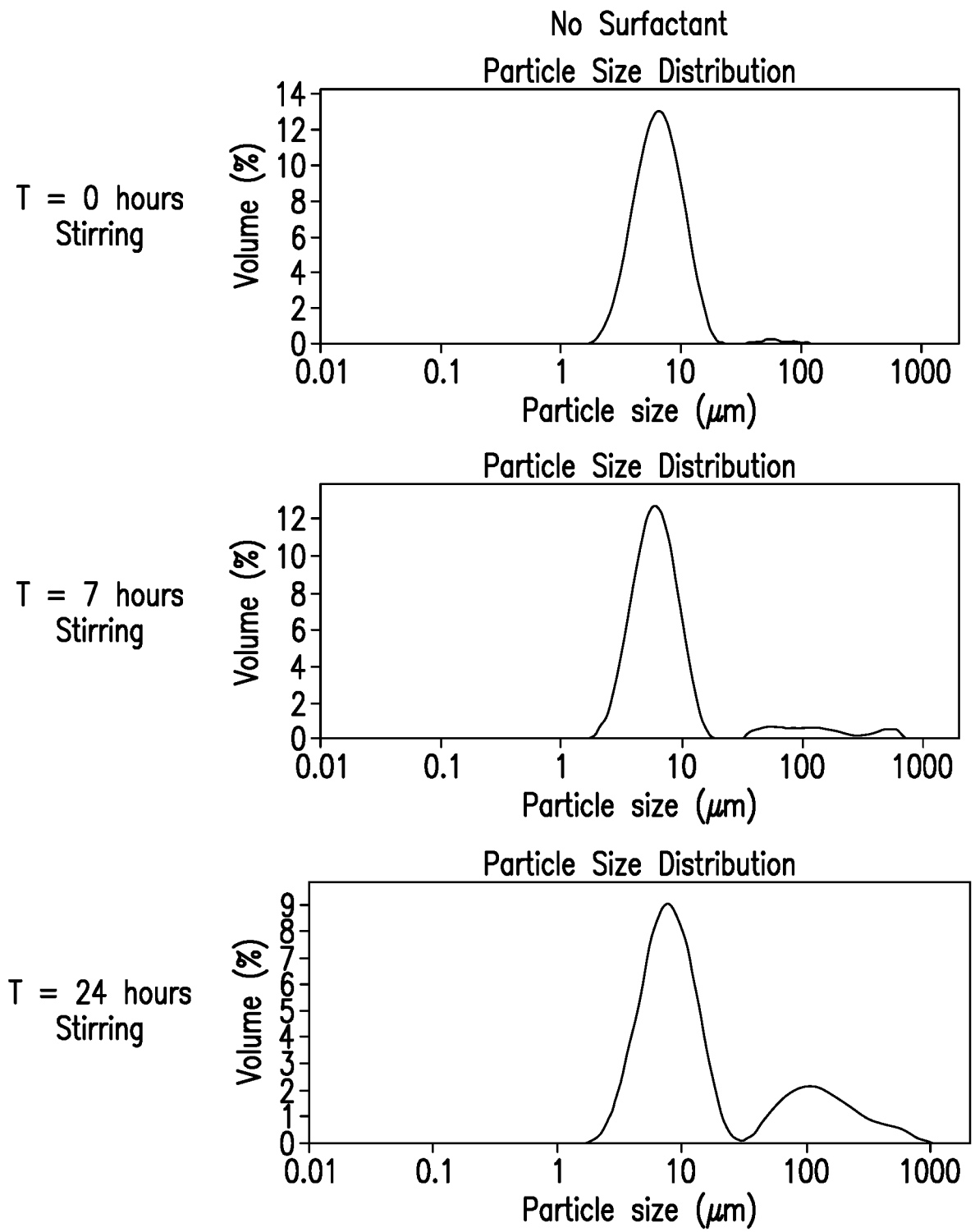

FIG. 6: Laboratory scale stirring study to evaluate the impact of time and stirring on the particle size distribution of a 15-valent pneumococcal polysaccharide (PnPs) conjugate formulation as measured by static light scattering (SLS). All 15 pneumococcal polysaccharide serotypes were conjugated to $CRM_{197}$ using reductive amination in aqueous solution. Conjugates were formulated in 20 mM L-histidine, pH 5.8, 150 mM NaCl and 0.25 mg/mL (w/v $Al^{+3}$) APA for the stirring study.

Figure 7:
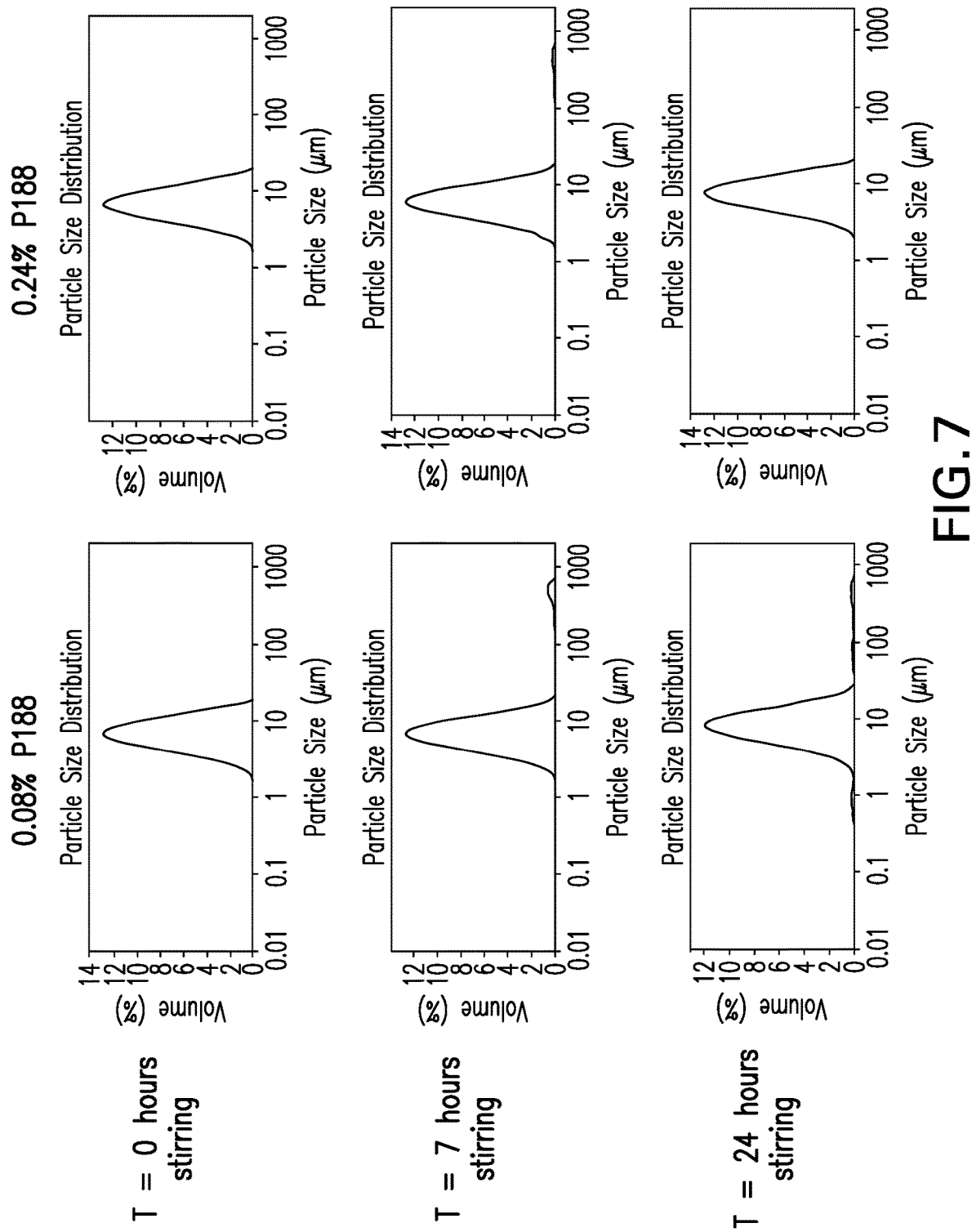

FIG. 7: Laboratory scale stirring study to evaluate of the impact of time and stirring on particle size distribution of 15-valent pneumococcal polysaccharide conjugate formulations as measured by SLS. All 15 pneumcoccal polysaccharide serotypes were conjugated to $CRM_{197}$ using reductive amination in aqueous solution. Conjugates were formulated for the stirring study in 20 mM L-histidine, pH 5.8, 150 mM NaCl and 0.25 mg/mL (w/v $Al^{+3}$) APA with either 0.08% w/v or 0.24% w/v poloxamer 188 (P188).

Figure 8A:
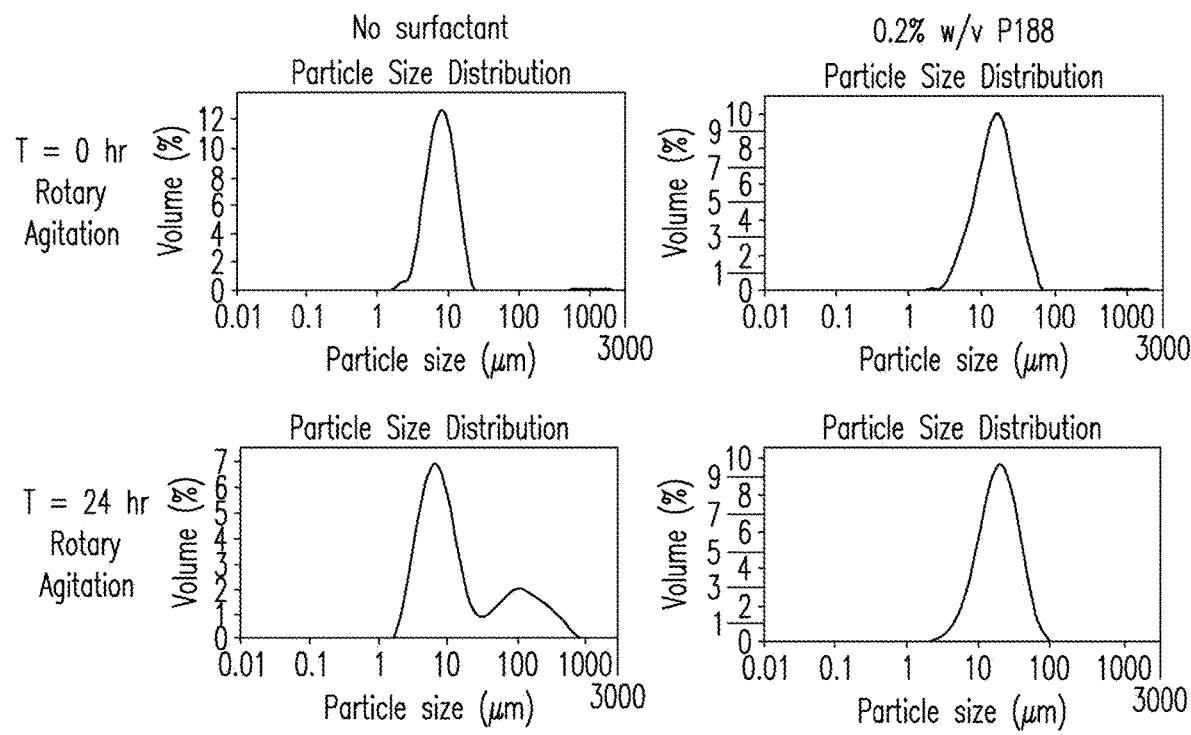
Figure 8B:
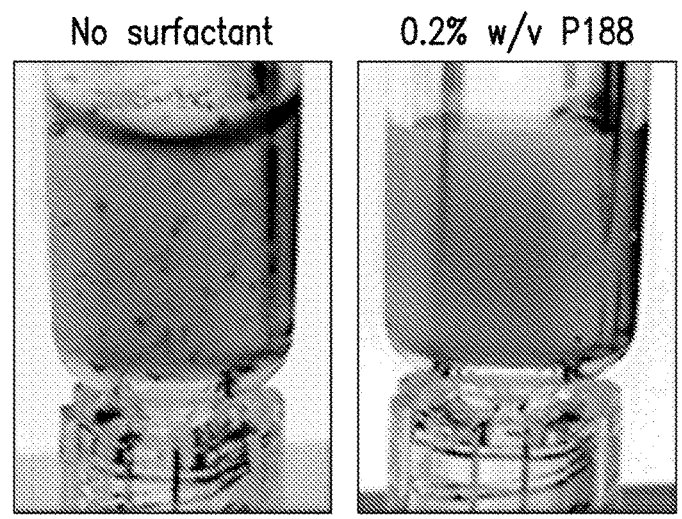

FIG. 8A-B: Laboratory scale simulated shipping and handling study of 15-valent pneumococcal polysaccharide conjugate formulations in syringes. All 15 pneumococcal polysaccharide serotypes were conjugated to $CRM_{197}$ using reductive amination in aqueous solution. Conjugates were formulated in 20 mM L-histidine, pH 5.8, 150 mM NaCl and 0.25 mg/mL (w/v $Al^{+3}$) APA without P188 or with 0.2% w/v P188. Particle size distribution as measured by SLS prior to and after 24 hours of horizontal rotation (A) and visual assessment of syringes after 24 hours of horizontal rotation (B) are shown.

Figure 9:
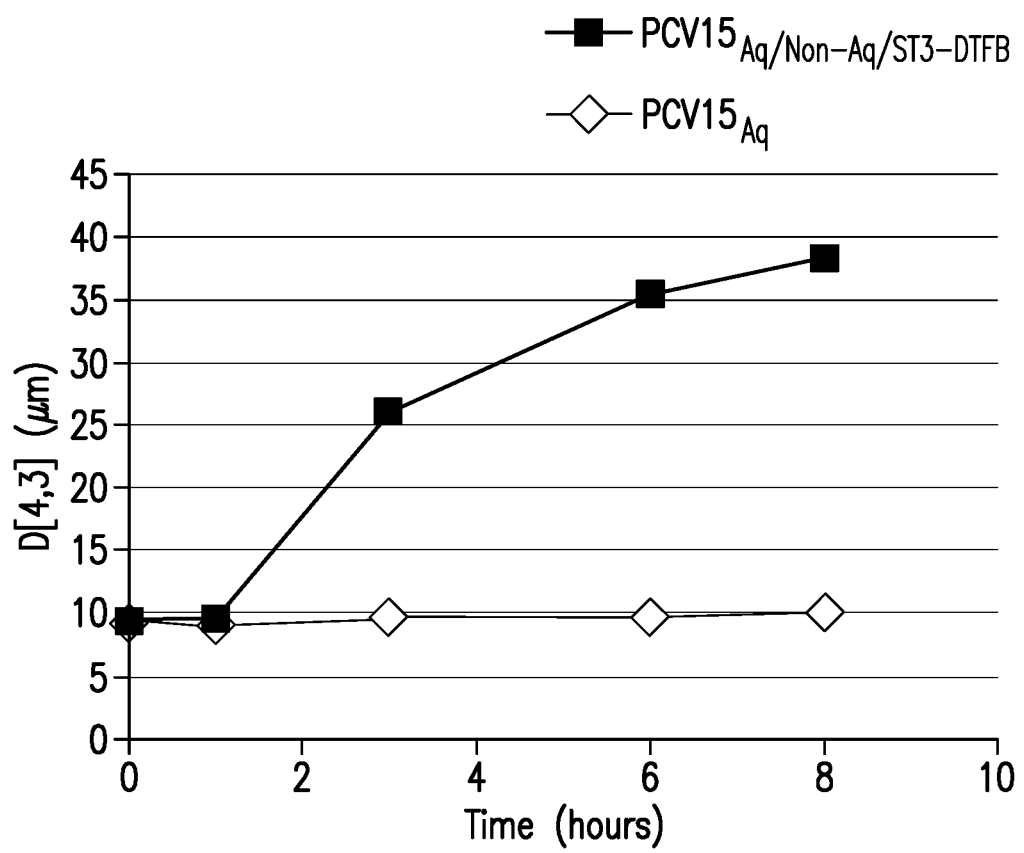

FIG. 9: Particle size distributions (expressed as a volume-weighted distribution or D[4,3] as measured by SLS) of two 15-valent pneumococcal polysaccharide conjugate formulations with 20 mM L-histidine, pH 5.8, 150 mM NaCl, 0.25 mg/mL (w/v $Al^{+3}$) APA, and 0.2% w/v P188. Formulation $PCV15_{Aq}$ was comprised of pneumcoccal polysaccharide-$CRM_{197}$ conjugates, generated by reductive amination in aqueous solution. Formulation $PCV15_{Aq/Non-Aq/ST3-DTFB}$ used a combination of 15 pneumococcal polysaccharide conjugates, some generated by reductive amination in aqueous solution and others by reductive amination in non-aqueous solution; all pneumococcal polysaccharide serotypes in $PCV15_{Aq/Non-Aq/ST3-DTFB}$ were conjugated to $CRM_{197}$ except for serotype 3 (ST3), which was conjugated to DTFB. Formulations were filled into syringes and horizontally agitated for up to 24 hours at 4° C. prior to SLS evaluation.

Figure 10A:
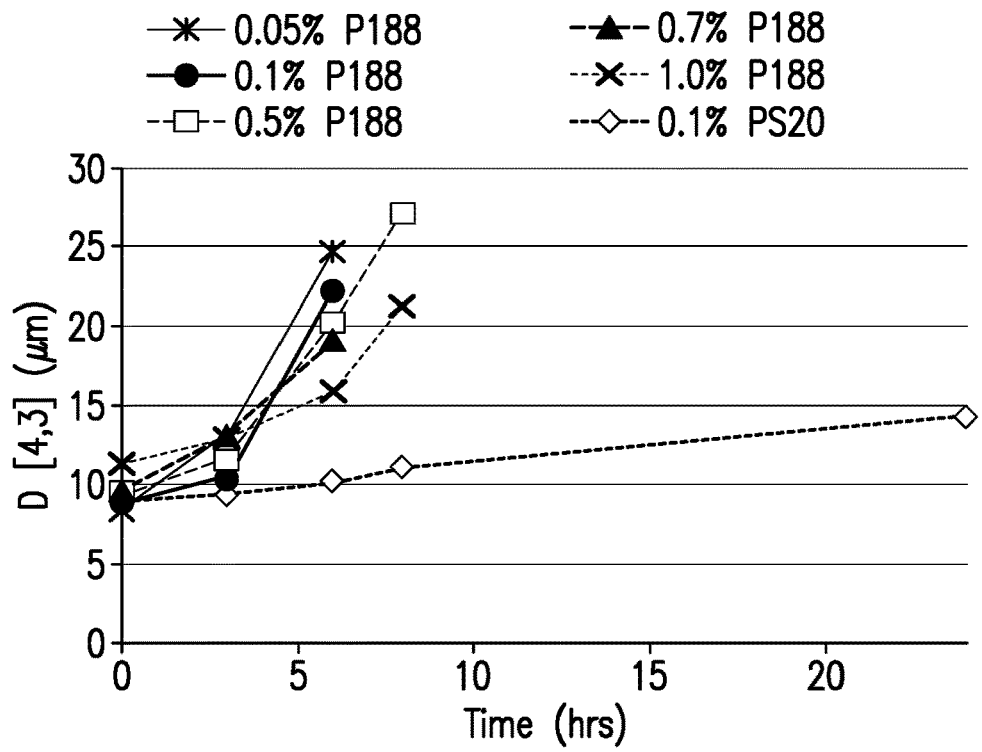
Figure 10B:
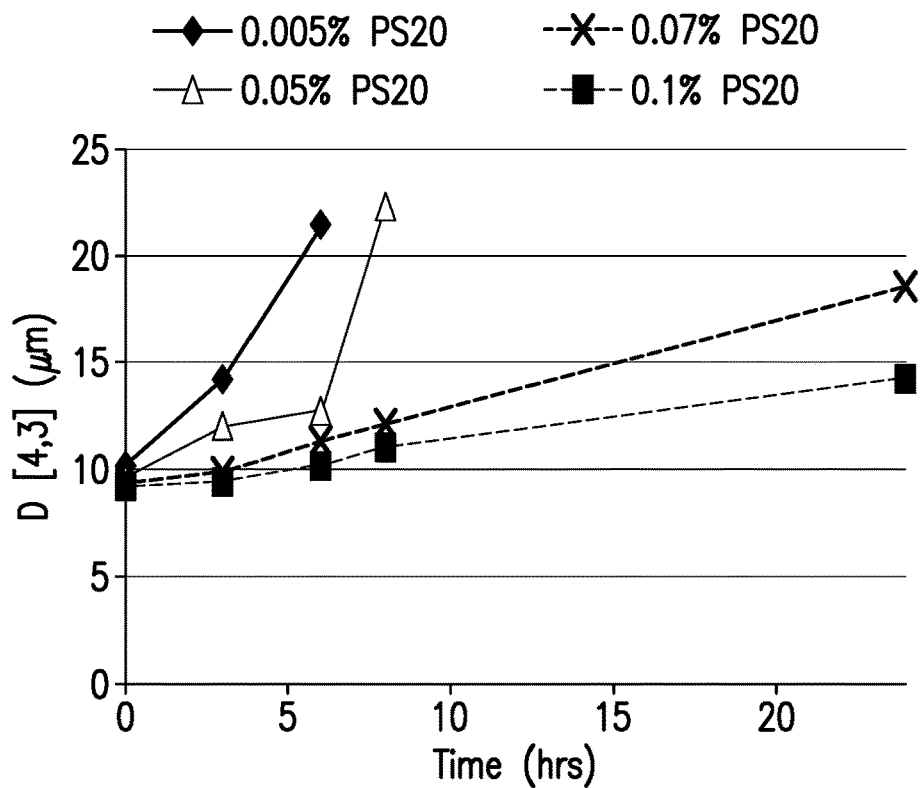

FIGS. 10A-B: D[4,3] values as measured by SLS of $PCV15_{Aq/Non-Aq/ST3-DTFB}$ formulations containing different concentrations of P188 (A) or PS-20 (A, B) after stirring and up to 24 hours of horizontal rotation in 1.5 mL HyPak syringes.

Figure 11:
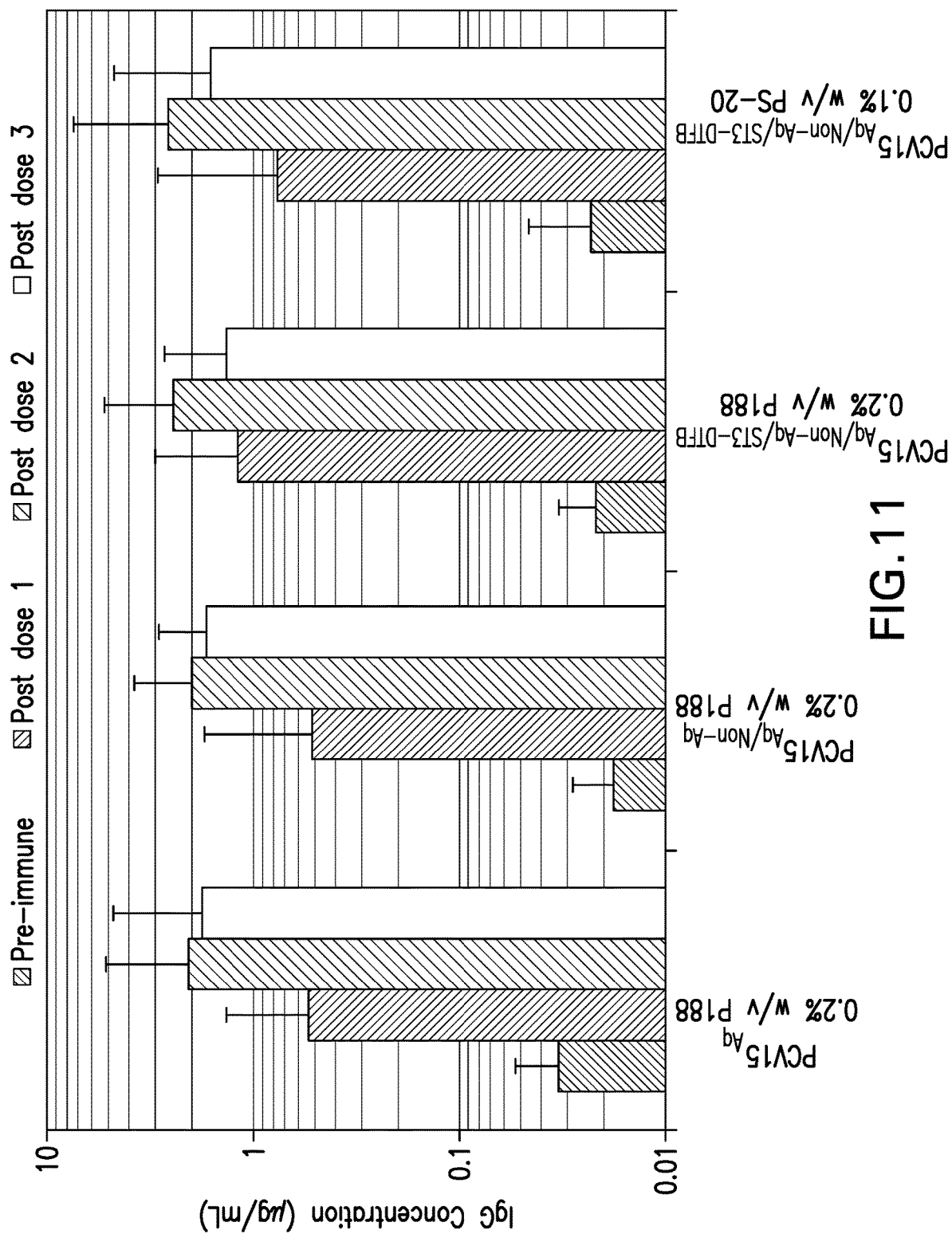

FIG. 11: Pneumococcal serotype 3-specific IgG concentrations from Infant Rhesus Monkeys (IRM) immunized with 15-valent pneumococcal polysaccharide conjugate formulations with aluminum phosphate adjuvant (APA). All formulations contained *S. pneumoniae* serotype 3 capsular polysaccharide (ST3) conjugated to either $CRM_{197}$ or DTFB. Formulation $PCV15_{Aq/Non-Aq}$ used a combination of 15 pneumococcal polysaccharide-$CRM_{197}$ conjugates, some generated by reductive amination in aqueous solution and others by reductive amination in non-aqueous solution. PCV15 formulations contained 0.2% w/v P188 or 0.1% w/v PS-20 as noted in figure.

Figure 12:
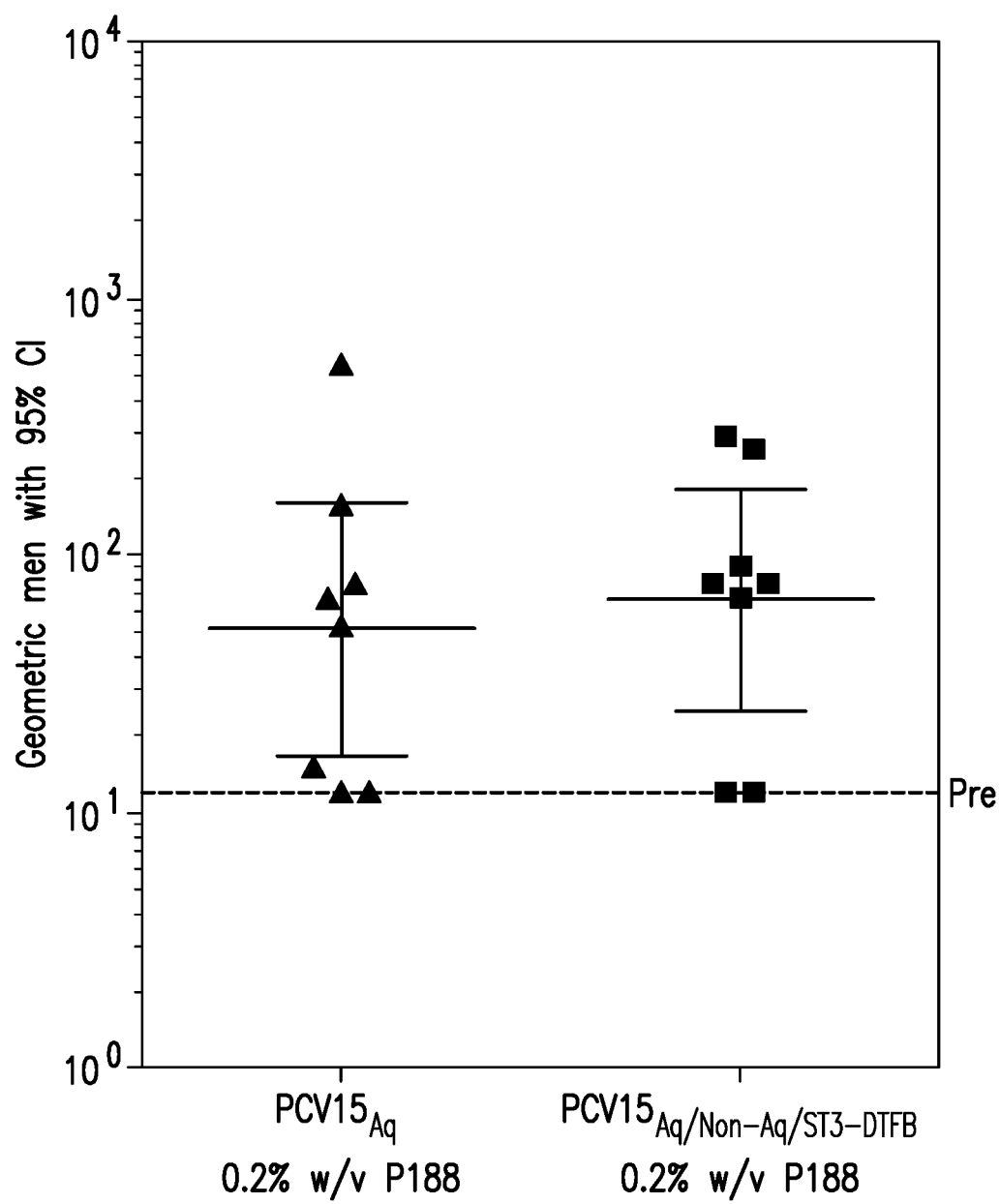

FIG. 12: Serotype 3 OPA (OPK) titers for Infant Rhesus Monkeys immunized with two 15-valent pneumococcal polysaccharide conjugate vaccines formulated with aluminum phosphate adjuvant (APA) and 0.2% w/v P188. The formulations contained *S. pneumoniae* serotype 3 capsular polysaccharide (ST3) conjugated to either $CRM_{197}$ ($PCV15_{Aq}$) or DTFB ($PCV15_{Aq/Non-Aq/ST3-DTFB}$).

Figure 13A:
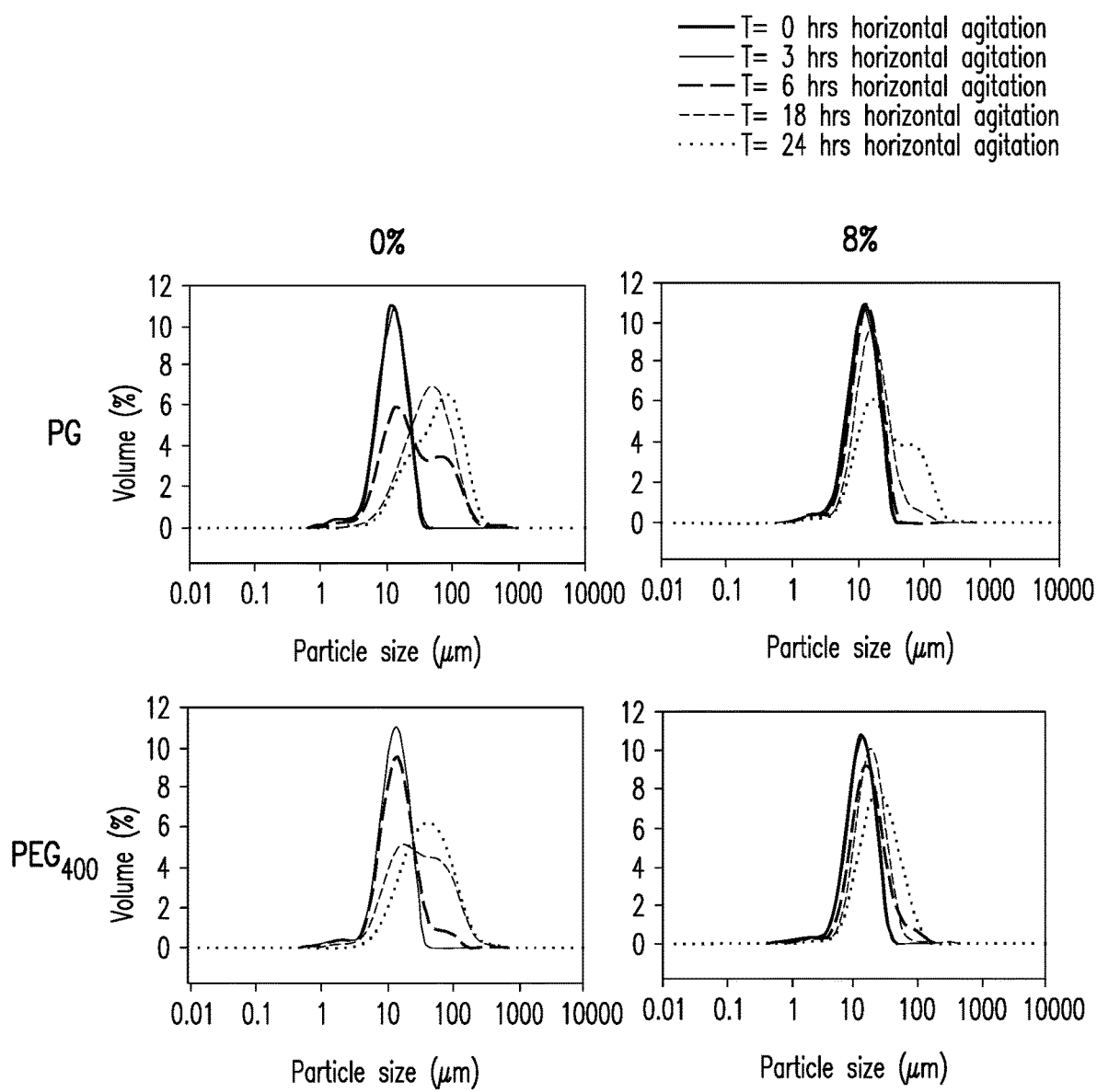
Figure 13B:
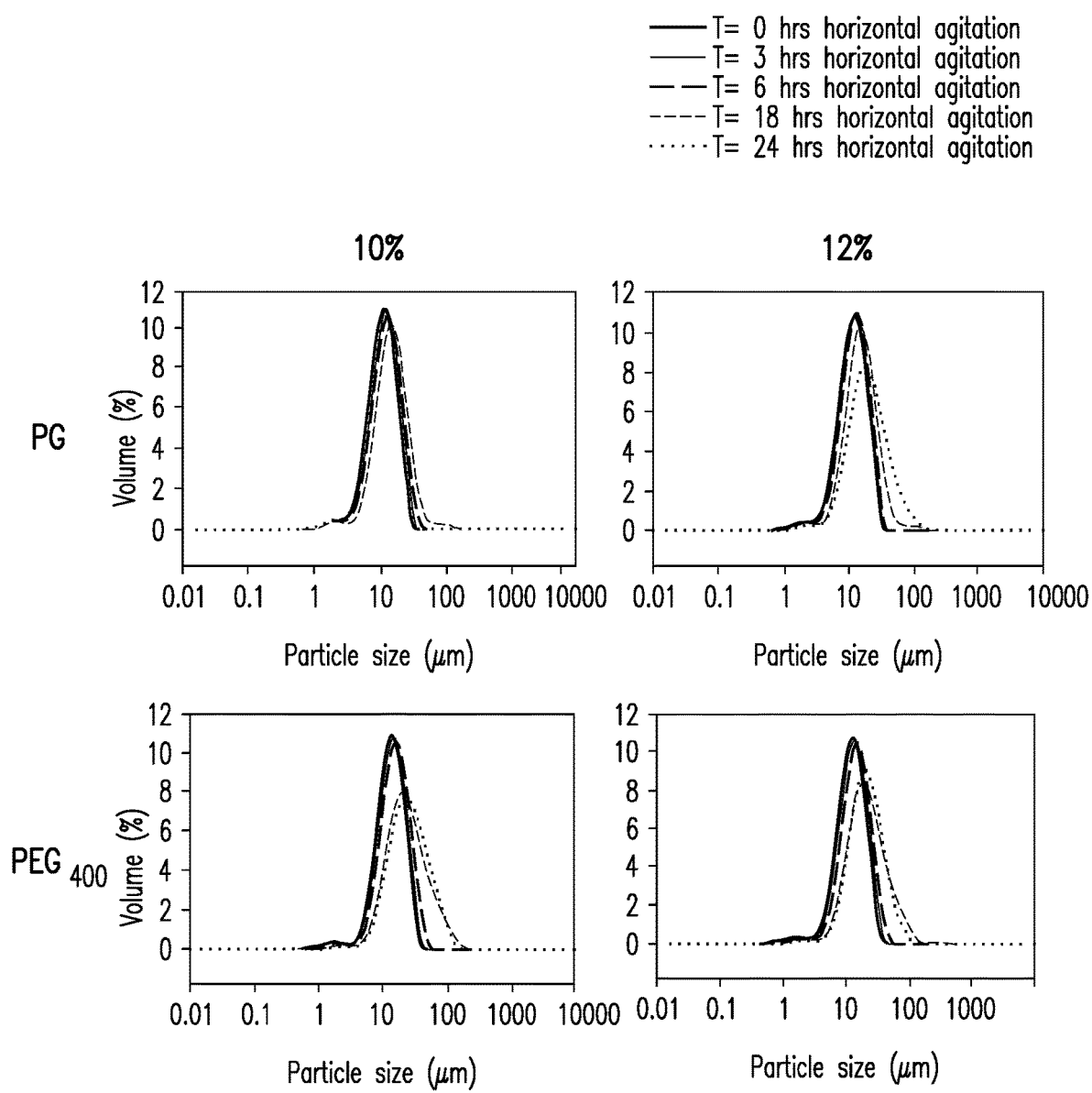
Figure 13C:
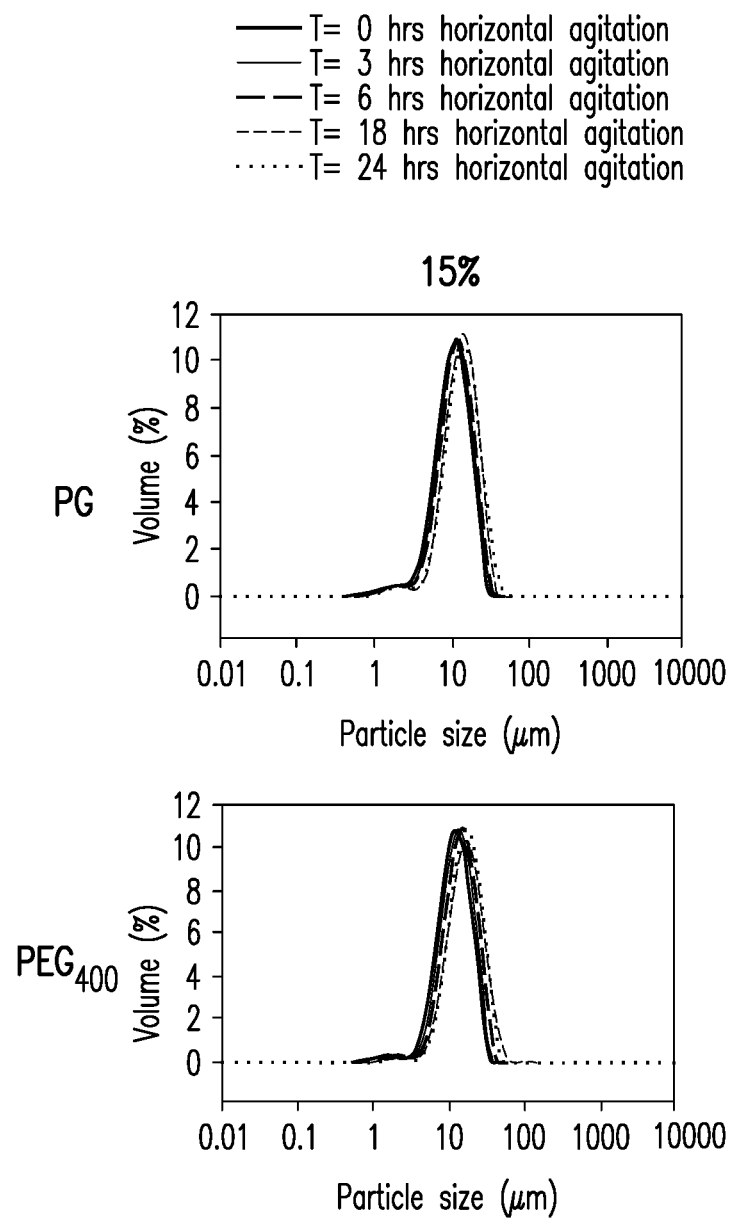

FIGS. 13A-C: Particle size distribution as measured by SLS of $PCV15_{Aq/Non-Aq/ST3-DTFB}$ formulations after 1 hour of stirring and upto 24 hours of horizontal rotation. Formulations contained 0.2% w/v poloxamer 188 and various concentrations (A: 0% and 8%; B: 10% and 12%; and C: 15%) of propylene glycol (PG) or polyethylene glycol 400 ($PEG_{400}$) as noted in figures.

Figure 14A:
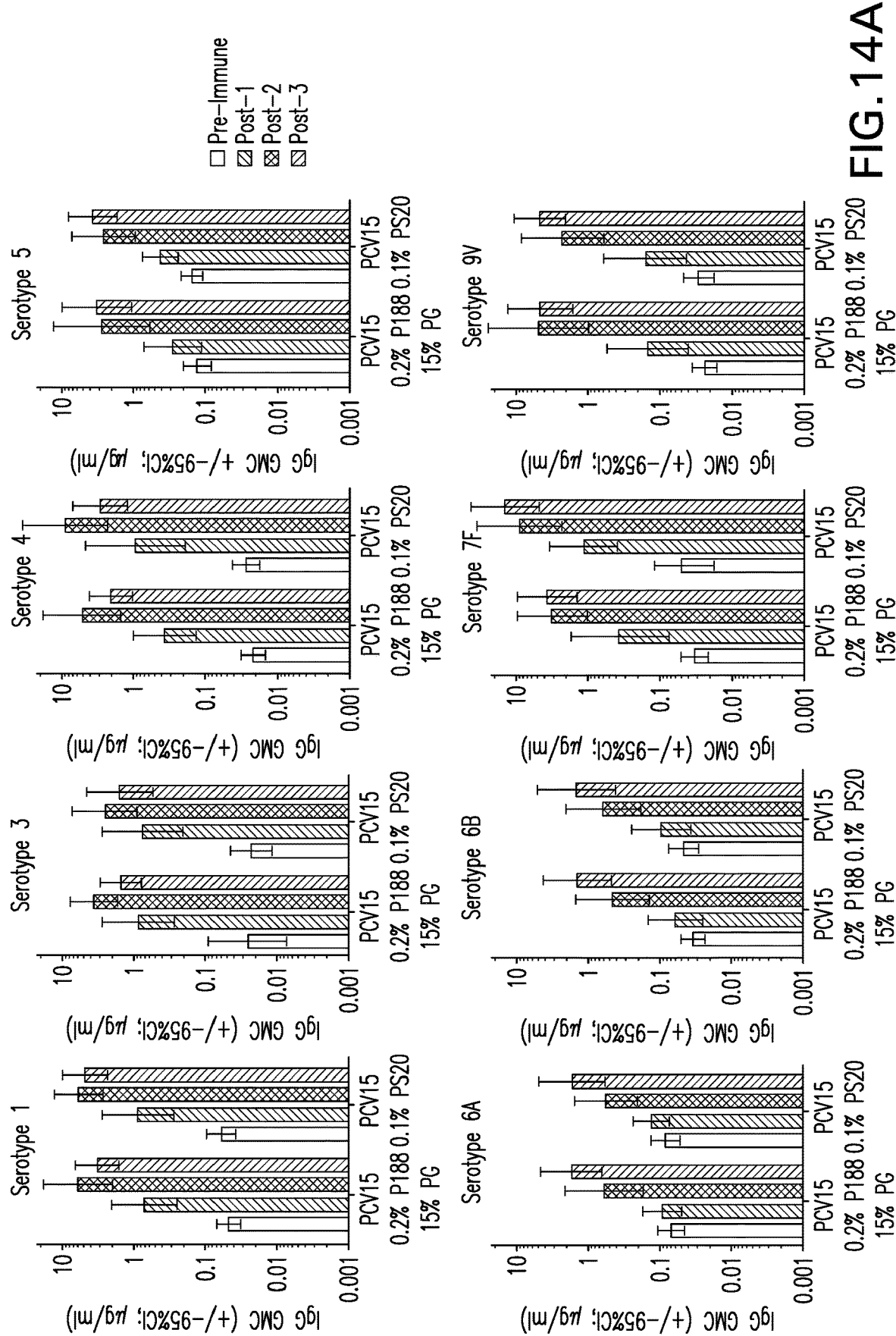
Figure 14B:
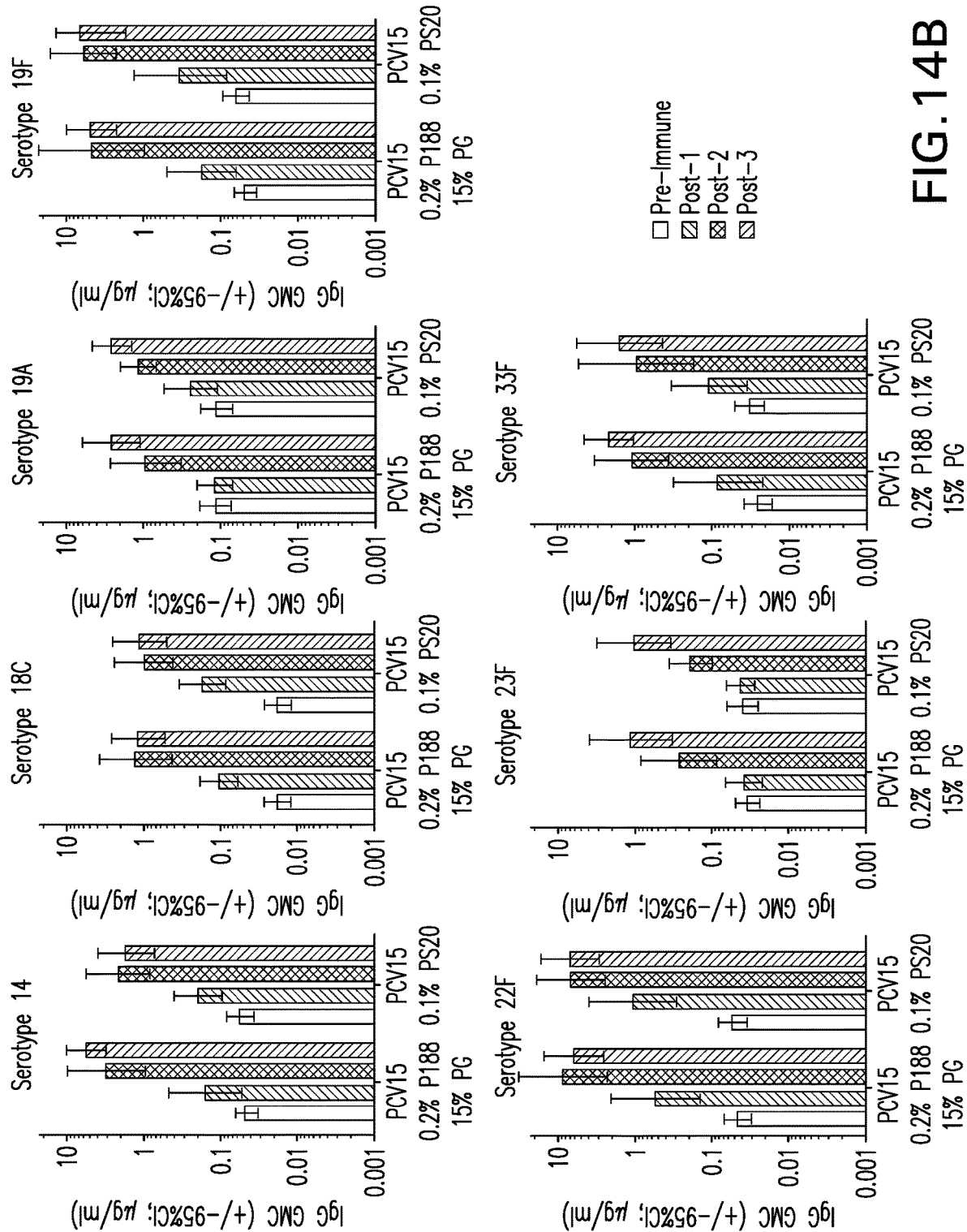

FIGS. 14A-B: Immunogenicity comparison study in Infant Rhesus Monkeys for $PCV15_{Aq/Non-AQ/ST3-DTFB}$ formulations containing either 0.2% w/v P188 with 15% w/v PG or 0.1% w/v PS-20 as described in Example 12. Eight animals per group received an intramuscular injection with either of the two formulations at T=0 (Dose 1), 1 month (Dose 2) and 2 months (Dose 3) of age. Serum was collected prior to Dose 1 and 2 weeks post dose 1, 2, and 3. The serotype-specific IgG concentrations (IgG GMC) from the pre-immune, post dose-1, post dose-2, and post dose-3 serum samples were measured as described in Example 10. Panel A shows immunogenicity results for serotypes 1, 3, 4, 5, 6A, 6B, 7F and 9V. Panel B shows immunogenicity results for serotype 14, 18C, 19A, 19F, 22F, 23F, and 33F.

DETAILED DESCRIPTION OF THE INVENTION

The present invention is based, in part, on the discovery that Diphtheria Toxin Fragment B can be isolated and used as a carrier protein for antigens such as polysaccharides. Historically, DTFB has been difficult to isolate because of its precipitation instability and difficulty in solubilizing (see e.g., Gill et al., 1971, J Biol Chem 246:1485).

As used herein, the term "polysaccharide" (Ps) is meant to include any antigenic saccharide element (or antigenic unit) commonly used in the immunologic and bacterial vaccine arts, including, but not limited to, a "saccharide", an "oligosaccharide", a "polysaccharide", a "liposaccharide", a "lipo-oligosaccharide (LOS)", a "lipopolysaccharide (LPS)", a "glycosylate", a "glycoconjugate" and the like.

As used herein, the term "comprises" when used with the immunogenic composition of the invention refers to the inclusion of any other components (subject to limitations of "consisting of" language for the antigen mixture), such as adjuvants and excipients. The term "consisting of" when used with the multivalent polysaccharide-protein conjugate mixture refers to a mixture having those particular S pneumoniae polysaccharide protein conjugates and no other S. pneumoniae polysaccharide protein conjugates from a different serotype.

As defined herein, the terms "precipitation", "precipitate", "particulate formation", "clouding", and "aggregation" may be used interchangeably and are meant to refer to any physical interaction or chemical reaction which results in the agglomeration of a polysaccharide-protein conjugate. The process of aggregation (e.g., protein aggregation) may be induced by numerous physicochemical stresses, including heat, pressure, pH, agitation, shear forces, freeze-thawing, dehydration, heavy metals, phenolic compounds, silicon oil, denaturants and the like.

As defined herein, a "surfactant" of the present invention is any molecule or compound that lowers the surface tension of an immunogenic composition formulation. A "surfactant system" comprises a surfactant but may allow for the inclusion of additional excipients such as polyols that increase the effects of the surfactant.

Diphtheria Toxin, an exotoxin secreted by *Corynebacterium diphtheriae*, is a classic A-B toxin composed of two subunits (fragments) linked by disulfide bridges and having three domains. Fragment A (DTFA) contains the ADP-ribose catalytic C domain, while Fragment B (DTFB) contains the central translocation T domain and a carboxy terminal receptor-binding R domain. DTFB is the non-toxic moiety constituting approximately 60% of the total amino acid sequence of DT. See e.g., Gill, D. M. and Dinius, L. L., *J. Biol. Chem.*, 246, 1485-1491 (1971), Gill, D. M. and Pappenheimer, Jr., A. M., *J. Biol. Chem.*, 246, 1492-1495 (1971), Collier, R. J. and Kandel, J., *J. Biol. Chem.*, 246, 1496-1503 (1971); and Drazin, R., Kandel, J., and Collier, R. J., *J. Biol. Chem.*, 246, 1504-1510 (1971).

The completed amino acid sequence of Diphtheria Toxin has been published. See Greenfield, L., Bjorn, M. J., Horn, G., Fong, D., Buck, G. A., Collier, R. J. and Kaplan, D. A., *Proc. Natl. Acad. Sci. USA* 80, 6853-6857 (1983). Specifically, DTFB comprises amino acid residues 194 to 535 of DT.

The $CRM_{197}$ carrier protein is a mutant form of DT that is rendered non-toxic by a single amino acid substitution in Fragment A at residue 52. $CRM_{197}$ and DT share complete sequence homology in Fragment B. Major T-cell epitopes were found predominantly in the B fragment of the DT amino acid sequence. See Bixler et al., Adv Exp Med Biol. (1989) 251:175-80; Raju et al., Eur. J. Immunol. (1995) 25: 3207-3214; Diethelm-Okita et al., J Infect Dis (2000) 181: 1001-9; and McCool et al., Infect. and Immun. 67 (September 1999), p. 4862-4869. Without being bound by any theory, Applicants hypothesized that the use of DTFB would improve polysaccharide immunogenicity relative to use of $CRM_{197}$ protein carrier, as more protein-derived putative immunodominant T-cell epitopes (per protein mass) are dosed in the DTFB conjugate, and more glycopeptides containing T-cell epitopes are dosed in the conjugate. The use of DTFB as a protein carrier has the added benefit that the absence of DT Fragment A avoids the inherent toxicity of DT and any potential residual toxicity on $CRM_{197}$.

Use of DTFB as described herein includes diphtheria toxin deletions of the ADP-ribosylation activity domain. Use of DTFB also includes variants having at least 90%, 95% or 99% sequence identity including deletions, substitutions and additions. An example of a variant is a deletion or mutation of the Cysteine 201. DTFB (C8) means diphtheria toxin deleted of the ADP-ribosylatin activation domain, and with cysteine 201 removed or mutated. Use of DTFB also includes fragments that cover sequence 265-450 of DT, which includes the published T-cell epitopes (See Bixler et al., Adv Exp Med Biol. (1989) 251:175-80; Raju et al., Eur. J. Immunol. (1995) 25: 3207-3214). DTFB also includes states of monomer, dimer, or oligomers. Use of DTFB also includes any protein complex (excluding full length DT or $CRM_{197}$), hybrid proteins, or conjugated proteins that contain the DTFB or fragments. Use of DTFB also includes chemically modified DTFB or fragments (i.e. pegylation, unnatural amino acid modification).

In certain embodiments, the DTFB is produced from enzymatic digestion and reduction of the native DT or the mutant $CRM_{197}$ with subsequent purification by adsorptive chromatography. Thus, it is envisioned that a purified DTFB, with or without a mutation at the DT C201 residue, could be prepared similarly from full length native or C201-mutated DT or $CRM_{197}$, or from variants thereof in which the A-fragment is truncated. It is specifically known that multimodal resins marketed as Capto™ Adhere and Capto™ MMC and Tris concentrations in excess of 50 mM during the chromatography cycle provide exceptional modes of purifying the cleaved native DTFB.

In certain embodiments of the invention, the preparation of DTFB includes up to 10 mM DTT. DTT prevents dimerization caused by disulfide bond formation between DTFB monomers due to free cysteine at residue position 201. In such cases, nickel is not added to the conjugation reaction mixture. However, the conjugation reaction proceeds by the same method otherwise. In a case where DTT is not used, dimerized DTFB may be conjugated to Ps and nickel, in a preferred embodiment, would be added to sequester residual, inhibitory cyanide to improve the extent of conjugation.

The removal of free cysteine (mutation of the DT C201) in the DTFB is expected to give similar behavior in the multimodal resins. Removal of the free cysteine is expected to eliminate the need for DTT since dimerization by disulfide bond formation between free cysteine would not be feasible. Increasing the Tris buffer concentration and the sodium chloride elution buffer concentration has been demonstrated to improve the recovery of DTFB protein from the Capto MMC chromatography resin. It is expected that the DTFB purification can be achieved using other multimodal resins.

In certain embodiments, the DTFB is expressed recombinantly with or without the mutation of the DT C201 residue and subsequently purified by various techniques known to those skilled in the art.

DTFB and variants thereof can be used as a carrier protein for antigens, including protein (peptides) and saccharides. In certain embodiments of the invention, the antigen is a saccharide from an encapsulated bacteria. In such vaccines, the saccharides are composed of long chains of sugar molecules that resemble the surface of certain types of bacteria. Encapsulated bacteria include, but are not limited to, *Streptococcus pneumoniae, Neisseria meningitides* and *Haemophilus influenzae* type b.

An immunogenic composition of the invention may be a multivalent composition containing one or more antigens conjugated to DTFB and one or more antigens conjugated to a second carrier. The antigens may be from the same organism or may be from different organisms. In preferred embodiments of the invention, the antigens are *Streptococcus pneumoniae* capsular polysaccharides.

Accordingly, in some embodiments, a second carrier is used for one or more of the antigens in a multivalent vaccine. The second carrier protein is preferably a protein that is non-toxic and non-reactogenic and obtainable in sufficient amount and purity. The second carrier protein is also conjugated or joined with an antigen, e.g., a *S. pneumoniae* polysaccharide to enhance immunogenicity of the antigen. Carrier proteins should be amenable to standard conjugation procedures. In one embodiment, each capsular polysaccharide not conjugated to the first carrier protein is conjugated to the same second carrier protein (e.g., each capsular polysaccharide molecule being conjugated to a single carrier protein). In another embodiment, the capsular polysaccharides not conjugated to the first carrier protein are conjugated to two or more carrier proteins (each capsular polysaccharide molecule being conjugated to a single carrier protein). In such embodiments, each capsular polysaccharide of the same serotype is typically conjugated to the same carrier protein.

In a particular embodiment of the present invention, $CRM_{197}$ is used as the second carrier protein. $CRM_{197}$ is a non-toxic variant (i.e., toxoid) of diphtheria toxin. In one embodiment, it is isolated from cultures of *Corynebacterium diphtheria* strain C7 (β197) grown in casamino acids and yeast extract-based medium. In another embodiment, $CRM_{197}$ is prepared recombinantly in accordance with the methods described in U.S. Pat. No. 5,614,382. Typically, $CRM_{197}$ is purified through a combination of ultra-filtration, ammonium sulfate precipitation, and ion-exchange chromatography. In some embodiments, $CRM_{197}$ is prepared in *Pseudomonas fluorescens* using Pfenex Expression Technology™ (Pfenex Inc., San Diego, Calif.).

Other suitable carrier proteins include additional inactivated bacterial toxins such as DT (Diphtheria toxoid), TT (tetanus toxid) or fragment C of TT, pertussis toxoid, cholera toxoid (e.g., as described in International Patent Application Publication No. WO 2004/083251), *E. coli* LT (heat-labile enterotoxin), *E. coli* ST (heat-stable enterotoxin), and exotoxin A from *Pseudomonas aeruginosa*. Bacterial outer membrane proteins such as outer membrane complex c (OMPC), porins, transferrin binding proteins, pneumococcal surface protein A (PspA; See International Application Patent Publication No. WO 02/091998), pneumococcal adhesin protein (PsaA), C5a peptidase from Group A or Group B *Streptococcus*, or *Haemophilus influenzae* protein D, pneumococcal pneumolysin (Kuo et al., 1995, Infect Immun 63; 2706-13) including ply detoxified in some fashion for example dPLY-GMBS (See International Patent Application Publication No. WO 04/081515) or dPLY-formol, PhtX, including PhtA, PhtB, PhtD, PhtE and fusions of Pht proteins for example PhtDE fusions, PhtBE fusions (See International Patent Application Publication Nos. WO 01/98334 and WO 03/54007), can also be used. Other proteins, such as ovalbumin, keyhole limpet hemocyanin (KLH), bovine serum albumin (BSA) or purified protein derivative of tuberculin (PPD), PorB (from *N. meningitidis*), PD (*Haemophilus influenzae* protein D; see, e.g., European Patent No. EP 0 594 610 B), or immunologically functional equivalents thereof, synthetic peptides (See European Patent Nos. EP0378881 and EP0427347), heat shock proteins (See International Patent Application Publication Nos. WO 93/17712 and WO 94/03208), pertussis proteins (See International Patent Application Publication No. WO 98/58668 and European Patent No. EP0471177), cytokines, lymphokines, growth factors or hormones (See International Patent Application Publication No. WO 91/01146), artificial proteins comprising multiple human CD4+ T cell epitopes from various pathogen derived antigens (See Falugi et al., 2001, Eur J Immunol 31:3816-3824) such as N19 protein (See Baraldoi et al., 2004, Infect Immun 72:4884-7), iron uptake proteins (See International Patent Application Publication No. WO 01/72337), toxin A or B of *C. difficile* (See International Patent Publication No. WO 00/61761), and flagellin (See Ben-Yedidia et al., 1998, Immunol Lett 64:9) can also be used as carrier proteins.

Other DT mutants can be used as the second carrier protein, such as $CRM_{176}$, $CRM_{228}$, $CRM_{45}$ (Uchida et al., 1973, J Biol Chem 218:3838-3844); $CRM_9$, $CRM_{45}$, $CRM_{102}$, $CRM_{103}$ and $CRM_{107}$ and other mutations described by Nicholls and Youle in Genetically Engineered Toxins, Ed: Frankel, Maecel Dekker Inc, 1992; deletion or mutation of Glu-148 to Asp, Gln or Ser and/or Ala 158 to Gly and other mutations disclosed in U.S. Pat. Nos. 4,709,017 or 4,950,740; mutation of at least one or more residues Lys 516, Lys 526, Phe 530 and/or Lys 534 and other mutations disclosed in U.S. Pat. Nos. 5,917,017 or 6,455,673; or fragment disclosed in U.S. Pat. No. 5,843,711. Such DT mutants can also be used to make DTFB variants where the variants comprise the B fragment contain the epitiope regions.

In certain embodiments, the present invention provides multivalent pneumococcal vaccines having one or more polysaccharides from certain serotypes conjugated to DTFB and, optionally, additional seroptypes conjugated to $CRM_{197}$. In one embodiment of the invention, an immunogenic composition of the invention comprises capsular polysaccharides from 1 or more serotypes individually conjugated to a DTFB protein carrier or a mutant thereof. In one embodiment, the present invention provides an immunogenic composition comprising polysaccharide-protein conjugates comprising capsular polysaccharides from at least one of serotypes 1, 2, 3, 4, 5, 6A, 6B, 6C, 6D, 7B, 7C, 7F, 8, 9N, 9V, 10A, 11A, 12F, 14, 15A, 15B, 15C, 16F, 17F, 18C, 19A, 19F, 20, 21, 22A, 22F, 23A, 23B, 23F, 24F, 27, 28A, 31, 33F, 34, 35A, 35B, 35F, and 38 of *Streptococcus pneumoniae* conjugated to a first carrier protein selected from diphtheria toxin (DT) fragment B (DTFB) or a variant thereof, and a pharmaceutically acceptable carrier. In certain embodiments of the invention, the immunogenic composition comprises, consists essentially of, or consists of capsular polysaccharides from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44 serotypes individually conjugated to a DTFB protein carrier or a mutant thereof.

In certain embodiments, the immunogenic compositions described above optionally further comprise capsular polysaccharides from one additional S. pneumoniae serotype selected from at least one of 1, 2, 3, 4, 5, 6A, 6B, 6C, 6D, 7B, 7C, 7F, 8, 9N, 9V, 10A, 11A, 12F, 14, 15A, 15B, 15C, 16F, 17F, 18C, 19A, 19F, 20, 21, 22A, 22F, 23A, 23B, 23F, 24F, 27, 28A, 31, 33F, 34, 35A, 35B, 35F, and 38 conjugated to a second carrier protein (which is distinct in at least one amino acid from the first carrier protein). Preferably, saccharides from a particular serotype are not conjugated to more than one carrier protein.

In certain embodiments of the invention, the immunogenic composition of the invention further comprises capsular polysaccharides from at least one additional serotype conjugated to a second carrier protein. In these embodiments, the immunogenic composition comprises, consists essentially of, or consists capsular polysaccharides from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44 serotypes individually conjugated to a second carrier protein which is not DTFB protein carrier or a mutant thereof.

In certain embodiments of the invention, the immugenic composition comprises, consists essentially of, or consists of, capsular polysaccharides from N serotypes where N is 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44; and capsular polysaccharides from each of the N serotypes are conjugated to the first protein carrier which is DTFB or a variant thereof. In other embodiments of the invention, capsular polysaccharides from 1, 2, 3 . . . or N−1 serotypes are conjugated to the first protein carrier, and capsular polysaccharides from N−1, N−2, N−3 . . . 1 serotypes are conjugated to the second protein carrier which is different from DTFB or a variant thereof.

In one specific embodiment of the invention, the present invention provides a 15-valent immunogenic composition comprising, consisting essentially of, or consisting of capsular polysaccharides from serotype 3 conjugated to DTFB or DTFB C8, and capsular polysaccharides from each of serotypes 1, 4, 5, 6A, 6B, 7F, 9V, 14, 18C, 19A, 19F, 22F, 23F, and 33F conjugated to $CRM_{197}$.

Capsular polysaccharides from Steptococcus pneumoniae can be prepared by standard techniques known to those skilled in the art. For example, polysaccharides can be isolated from bacteria and may be sized to some degree by known methods (see, e.g., European Patent Nos. EP497524 and EP497525); and preferably by microfluidisation accomplished using a homogenizer or by chemical hydrolysis. In one embodiment, S. pneumoniae strains corresponding to each polysaccharide serotype are grown in a soy-based medium. The individual polysaccharides are then purified through standard steps including centrifugation, precipitation, and ultra-filtration. See, e.g., U.S. Patent Application Publication No. 2008/0286838 and U.S. Pat. No. 5,847,112. Polysaccharides can be sized in order to reduce viscosity and/or to improve filterability of subsequent conjugated products. In the present invention, capsular polysaccharides are prepared from one or more of serotypes 1, 2, 3, 4, 5, 6A, 6B, 6C, 6D, 7B, 7C, 7F, 8, 9N, 9V, 10A, 11A, 12F, 14, 15A, 15B, 15C, 16F, 17F, 18C, 19A, 19F, 20, 21, 22A, 22F, 23A, 23B, 23F, 24F, 27, 28A, 31, 33F, 34, 35A, 35B, 35F, and 38.

The purified polysaccharides are chemically activated to introduce functionalities capable of reacting with the carrier protein. Once activated, each capsular polysaccharide is separately conjugated to a carrier protein to form a glycoconjugate. The polysaccharide conjugates may be prepared by known coupling techniques.

In one embodiment, the chemical activation of the polysaccharides and subsequent conjugation to the carrier protein are achieved by means described in U.S. Pat. Nos. 4,365,170, 4,673,574 and 4,902,506. Briefly, the pneumococcal polysaccharide is reacted with a periodate-based oxidizing agent such as sodium periodate, potassium periodate, or periodic acid resulting in random oxidative cleavage of vicinal hydroxyl groups to generate reactive aldehyde groups.

Direct aminative coupling of the oxidized polysaccharide to primary amine groups on the protein carrier (mainly lysine residues) can be accomplished by reductive amination. For example, conjugation is carried out by reacting a mixture of the activated polysaccharide and carrier protein with a reducing agent such as sodium cyanoborohydride in the presence of nickel. The conjugation reaction may be carried out in aqueous solution or in an organic solvent such as dimethylsulfoxide (DMSO). See, e.g., US2015/0231270 A1, EP 0471 177 B1, US2011/0195086 A1. At the conclusion of the conjugation reaction, unreacted aldehydes are capped by addition of a strong reducing agent, such as sodium borohydride.

In one embodiment, prior to formulation, each pneumococcal capsular polysaccharide antigen is individually purified from S. pneumoniae, activated to form reactive aldehydes, and then covalently conjugated using reductive amination with sodium cyanoboroydride in the presence of nickel to the first or second carrier protein. Nickel complexes with residual, inhibitory cyanide from sodium cyanoborohydride reducing agent used for reductive amination.

In certain embodiments, the conjugation reaction is performed by reductive amination wherein nickel is used for greater conjugation reaction efficiency and to aid in free cyanide removal. Transition metals are known form stable complexes with cyanide and are known to improve reductive methylation of protein amino groups and formaldehyde with sodium cyanoborohydride (Gidley et al., 1982, Biochem J. 203: 331-334; Jentoft et al., 1980, Anal Biochem. 106: 186-190). By complexing residual, inhibitory cyanide, the addition of nickel increases the consumption of protein during the conjugation of and leads to formation of larger, potentially more immungenic conjugates.

Variability in free cyanide levels in commercial sodium cyanoborohydride reagent lots may lead to inconsistent conjugation performance, resulting in variable conjugate attributes, including molecular mass and polysaccharide-to-protein ratio. The addition of nickel to the conjugation reaction reduces the level of free cyanide and thus improves the degree of lot-to-lot conjugate consistency.

In another embodiment, the conjugation method may employ activation of polysaccharide with 1-cyano-4-dimethylamino pyridinium tetrafluoroborate (CDAP) to form a cyanate ester. The activated saccharide may be coupled directly to an amino group on the carrier protein.

In another embodiment, a reactive homobifunctional or heterobifunctional group may be introduced on the activated polysaccharide by reacting the cyanate ester with any of several available modalities. For example, cystamine or cysteamine may be used to prepare a thiolated polysaccharide which could be coupled to the carrier via a thioether linkage obtained after reaction with a maleimide-activated carrier protein (for example using GMBS) or a haloacetylated carrier protein (for example using iodoacetimide [e.g. ethyl iodoacetimide HCl] or N-succinimidyl bromoacetate or SIAB, or SIA, or SBAP). In a preferred embodiment, the cyanate ester is reacted with hexane diamine or adipic acid dihydrazide (ADH) and the resultant amino-derivatised saccharide is conjugated to a free carboxy group on the carrier protein using carbodiimide (e.g. EDAC or EDC) chemistry. Such conjugates are described in International Patent Application Publication Nos. WO 93/15760, WO 95/08348 and WO 96/29094; and Chu et al., 1983, Infect. Immunity 40:245-256.

Other suitable conjugation methods use carbodiimides, hydrazides, active esters, norborane, p-nitrobenzoic acid, N-hydroxysuccinimide, S-NHS, EDC, TSTU. Many are described in International Patent Application Publication No. WO 98/42721. Conjugation may involve a carbonyl linker which may be formed by reaction of a free hydroxyl group of the saccharide with CDI (See Bethell et al., 1979, J. Biol. Chem. 254:2572-4; Hearn et al., 1981, J. Chromatogr. 218:509-18) followed by reaction with carrier protein to form a carbamate linkage. This chemistry consists of reduction of the anomeric terminus of a carbohydrate to form a primary hydroxyl group followed by reaction of the primary hydroxyl with CDI to form a carbamate intermediate and subsequent coupling to protein carrier amino groups. The reaction may require optional protection/deprotection of other primary hydroxyl groups on the saccharide.

Following conjugation, the polysaccharide-protein conjugates are purified to remove excess conjugation reagents as well as residual free protein and free polysaccharide by one or more of any techniques well known to the skilled artisan, including concentration/diafiltration operations, ultrafiltration, precipitation/elution, column chromatography, and depth filtration. See, e.g., U.S. Pat. No. 6,146,902.

After the individual glycoconjugates are purified, they are compounded to formulate the immunogenic composition of the present invention. These pneumococcal conjugates are prepared by separate processes and bulk formulated into a single dosage formulation.

Pharmaceutical/Vaccine Compositions

The present invention further provides compositions, including pharmaceutical, immunogenic and vaccine compositions, comprising, consisting essentially of, or alternatively, consisting of any of the polysaccharide serotype combinations described above together with a pharmaceutically acceptable carrier and an adjuvant. In one embodiment, the compositions comprise, consist essentially of, or consist of 2 to 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44 distinct polysaccharide-protein conjugates, wherein each of the conjugates contains a different capsular polysaccharide conjugated to either the first carrier protein or the second carrier protein, and wherein the capsular polysaccharides from at least one of serotypes 1, 2, 3, 4, 5, 6A, 6B, 6C, 6D, 7B, 7C, 7F, 8, 9N, 9V, 10A, 11A, 12F, 14, 15A, 15B, 15C, 16F, 17F, 18C, 19A, 19F, 20, 21, 22A, 22F, 23A, 23B, 23F, 24F, 27, 28A, 31, 33F, 34, 35A, 35B, 35F, and 38 of *Streptococcus pneumoniae* are conjugated to a first carrier protein selected from diphtheria toxin fragment B (DTFB) or a mutant thereof, and the remaining *S. pneumoniae* serotypes selected from serotypes 1, 2, 3, 4, 5, 6A, 6B, 6C, 6D, 7B, 7C, 7F, 8, 9N, 9V, 10A, 11A, 12F, 14, 15A, 15B, 15C, 16F, 17F, 18C, 19A, 19F, 20, 21, 22A, 22F, 23A, 23B, 23F, 24F, 27, 28A, 31, 33F, 34, 35A, 35B, 35F, and 38 are conjugated to a second carrier protein (which is distinct in at least one amino acid from the first carrier protein) together with a pharmaceutically acceptable carrier and an adjuvant.

Formulation of the polysaccharide-protein conjugates of the present invention can be accomplished using art-recognized methods. For instance, 15 individual pneumococcal conjugates can be formulated with a physiologically acceptable vehicle to prepare the composition. Examples of such vehicles include, but are not limited to, water, buffered saline, polyols (e.g., glycerol, propylene glycol, liquid polyethylene glycol) and dextrose solutions.

In a preferred embodiment, the vaccine composition is formulated in L-histidine buffer with sodium chloride.

As defined herein, an "adjuvant" is a substance that serves to enhance the immunogenicity of an immunogenic composition of the invention. An immune adjuvant may enhance an immune response to an antigen that is weakly immunogenic when administered alone, e.g., inducing no or weak antibody titers or cell-mediated immune response, increase antibody titers to the antigen, and/or lowers the dose of the antigen effective to achieve an immune response in the individual. Thus, adjuvants are often given to boost the immune response and are well known to the skilled artisan. Suitable adjuvants to enhance effectiveness of the composition include, but are not limited to:

(1) aluminum salts (alum), such as aluminum hydroxide, aluminum phosphate, aluminum sulfate, etc.;

(2) oil-in-water emulsion formulations (with or without other specific immunostimulating agents such as muramyl peptides (defined below) or bacterial cell wall components), such as, for example, (a) MF59 (International Patent Application Publication No. WO 90/14837), containing 5% Squalene, 0.5% TWEEN® 80, and 0.5% Span 85 (optionally containing various amounts of MTP-PE) formulated into submicron particles using a microfluidizer such as Model 110Y microfluidizer (Microfluidics, Newton, Mass.), (b) SAF, containing 10% Squalene, 0.4% TWEEN® 80, 5% pluronic-blocked polymer L121, and thr-MDP either microfluidized into a submicron emulsion or vortexed to generate a larger particle size emulsion, (c) Ribi™ adjuvant system (RAS), (Corixa, Hamilton, Mont.) containing 2% Squalene, 0.2% TWEEN® 80, and one or more bacterial cell wall components from the group consisting of 3-O-deaylated monophosphorylipid A (MPL™) described in U.S. Pat. No. 4,912,094, trehalose dimycolate (TDM), and cell wall skeleton (CWS), preferably MPL+CWS (Detox™); and (d) a Montanide ISA;

(3) saponin adjuvants, such as Quil A or STIMULON™ QS-21 (Antigenics, Framingham, Mass.) (see, e.g., U.S. Pat. No. 5,057,540) may be used or particles generated therefrom such as ISCOM (immunostimulating complexes formed by the combination of cholesterol, saponin, phospholipid, and amphipathic proteins) and Iscomatrix® (having essentially the same structure as an ISCOM but without the protein);

(4) bacterial lipopolysaccharides, synthetic lipid A analogs such as aminoalkyl glucosamine phosphate compounds (AGP), or derivatives or analogs thereof, which are available from Corixa, and which are described in U.S. Pat. No. 6,113,918; one such AGP is 2-[(R)-3-tetradecanoyloxytetradecanoylamino]ethyl 2-Deoxy-4-O-phosphono-3-O—[(R)-3-tetradecanoyloxytetradecanoyl]-2-[(R)-3-tetradecanoyloxytetradecanoylamino]-b-D-glucopyranoside, which is also known as 529 (formerly known as RC529), which is formulated as an aqueous form or as a stable emulsion (5) synthetic polynucleotides such as oligonucleotides containing CpG motif(s) (U.S. Pat. No. 6,207,646); and (6) cytokines, such as interleukins (e.g., IL-1, IL-2, IL-4, IL-5, IL-6, IL-7, IL-12, IL-15, IL-18, etc.), interferons (e.g., gamma interferon), granulocyte macrophage colony stimulating factor (GM-CSF), macrophage colony stimulating factor (M-CSF), tumor necrosis factor (TNF), costimulatory molecules B7-1 and B7-2, etc; and (7) complement, such as a trimer of complement component C3d.

In another embodiment, the adjuvant is a mixture of 2, 3, or more of the above adjuvants, e.g., SBAS2 (an oil-in-water emulsion also containing 3-deacylated monophosphoryl lipid A and QS21).

Muramyl peptides include, but are not limited to, N-acetyl-muramyl-L-threonyl-D-isoglutamine (thr-MDP), N-acetyl-normuramyl-L-alanine-2-(1'-2' dipalmitoyl-sn-glycero-3-hydroxyphosphoryloxy)-ethylamine (MTP-PE), etc.

In certain embodiments, the adjuvant is an aluminum salt. The aluminum salt adjuvant may be an alum-precipitated vaccine or an alum-adsorbed vaccine. Aluminum-salt adjuvants are well known in the art and are described, for example, in Harlow, E. and D. Lane (1988; Antibodies: A Laboratory Manual Cold Spring Harbor Laboratory) and Nicklas, W. (1992; Aluminum salts. Research in Immunology 143:489-493). The aluminum salt includes, but is not limited to, hydrated alumina, alumina hydrate, alumina trihydrate (ATH), aluminum hydrate, aluminum trihydrate, Alhydrogel®, Superfos, Amphogel®, aluminum (III) hydroxide, aluminum hydroxyphosphate sulfate (Aluminum Phosphate Adjuvant (APA)), amorphous alumina, trihydrated alumina, or trihydroxyaluminum.

APA is an aqueous suspension of aluminum hydroxyphosphate. APA is manufactured by blending aluminum chloride and sodium phosphate in a 1:1 volumetric ratio to precipitate aluminum hydroxyphosphate. After the blending process, the material is size-reduced with a high-shear mixer to achieve a monodisperse particle size distribution. The product is then diafiltered against physiological saline and steam sterilized.

In certain embodiments, a commercially available Al(OH)$_3$ (e.g. Alhydrogel® or Superfos of Denmark/Accurate Chemical and Scientific Co., Westbury, N.Y.) is used to adsorb proteins in a ratio of 50-200 g protein/mg aluminum hydroxide. Adsorption of protein is dependent, in another embodiment, on the pI (Isoelectric pH) of the protein and the pH of the medium. A protein with a lower pI adsorbs to the positively charged aluminum ion more strongly than a protein with a higher pI. Aluminum salts may establish a depot of Ag that is released slowly over a period of 2-3 weeks, be involved in nonspecific activation of macrophages and complement activation, and/or stimulate innate immune mechanism (possibly through stimulation of uric acid). See, e.g., Lambrecht et al., 2009, Curr Opin Immunol 21:23.

Monovalent bulk aqueous conjugates are typically blended together and diluted. Once diluted, the batch is sterile filtered. Aluminum phosphate adjuvant is added aseptically to target a final concentration of 4 µg/mL for all serotypes except 6B, which is diluted to target 8 µg/mL, and a final aluminum concentration of 250 µg/mL. The adjuvanted, formulated batch will be filled into vials or syringes.

In certain embodiments, the adjuvant is a CpG-containing nucleotide sequence, for example, a CpG-containing oligonucleotide, in particular, a CpG-containing oligodeoxynucleotide (CpG ODN). In another embodiment, the adjuvant is ODN 1826, which may be acquired from Coley Pharmaceutical Group.

"CpG-containing nucleotide," "CpG-containing oligonucleotide," "CpG oligonucleotide," and similar terms refer to a nucleotide molecule of 6-50 nucleotides in length that contains an unmethylated CpG moiety. See, e.g., Wang et al., 2003, Vaccine 21:4297. In another embodiment, any other art-accepted definition of the terms is intended. CpG-containing oligonucleotides include modified oligonucleotides using any synthetic internucleoside linkages, modified base and/or modified sugar.

Methods for use of CpG oligonucleotides are well known in the art and are described, for example, in Sur et al., 1999, J Immunol. 162:6284-93; Verthelyi, 2006, Methods Mol Med. 127:139-58; and Yasuda et al., 2006, Crit Rev Ther Drug Carrier Syst. 23:89-110.

Administration/Dosage

The compositions and formulations of the present invention can be used to protect or treat a human susceptible to infection, e.g., a pneumococcal infection, by means of administering the vaccine via a systemic or mucosal route. In one embodiment, the present invention provides a method of inducing an immune response to a S. pneumoniae capsular polysaccharide conjugate, comprising administering to a human an immunologically effective amount of an immunogenic composition of the present invention. In another embodiment, the present invention provides a method of vaccinating a human against a pneumococcal infection, comprising the step of administering to the human an immunogically effective amount of an immunogenic composition of the present invention.

Optimal amounts of components for a particular vaccine can be ascertained by standard studies involving observation of appropriate immune responses in subjects. For example, in another embodiment, the dosage for human vaccination is determined by extrapolation from animal studies to human data. In another embodiment, the dosage is determined empirically. Infant Rhesus Monkey animal data provided in the Examples demonstrates that that the vaccine is immunogenic.

"Effective amount" of a composition of the invention refers to a dose required to elicit antibodies that significantly reduce the likelihood or severity of infectivitiy of a microbe, e.g., S. pneumoniae, during a subsequent challenge.

The methods of the invention can be used for the prevention and/or reduction of primary clinical syndromes caused by microbes, e.g., S. pneumoniae, including both invasive infections (meningitis, pneumonia, and bacteremia), and noninvasive infections (acute otitis media, and sinusitis).

Administration of the compositions of the invention can include one or more of: injection via the intramuscular, intraperitoneal, intradermal or subcutaneous routes; or via mucosal administration to the oral/alimentary, respiratory or genitourinary tracts. In one embodiment, intranasal administration is used for the treatment of pneumonia or otitis media (as nasopharyngeal carriage of pneumococci can be more effectively prevented, thus attenuating infection at its earliest stage).

The amount of conjugate in each vaccine dose is selected as an amount that induces an immunoprotective response without significant, adverse effects. Such amount can vary depending upon the pneumococcal serotype. Generally, for polysaccharide-based conjugates, each dose will comprise 0.1 to 100 µg of each polysaccharide, particularly 0.1 to 10 µg, and more particularly 1 to 5 µg. For example, each dose can comprise 100, 150, 200, 250, 300, 400, 500, or 750 ng or 1, 1.5, 2, 3, 4, 5, 6, 7, 7.5, 8, 9, 10, 11, 12, 13, 14, 15, 16, 18, 20, 22, 25, 30, 40, 50, 60, 70, 80, 90, or 100 µg.

Optimal amounts of components for a particular vaccine can be ascertained by standard studies involving observation of appropriate immune responses in subjects. For example, in another embodiment, the dosage for human vaccination is determined by extrapolation from animal studies to human data. In another embodiment, the dosage is determined empirically.

In one embodiment, the dose of the aluminum salt is 10, 15, 20, 25, 30, 50, 70, 100, 125, 150, 200, 300, 500, or 700 µg, or 1, 1.2, 1.5, 2, 3, 5 mg or more. In yet another embodiment, the dose of aluminum salt described above is per µg of recombinant protein.

In a particular embodiment of the present invention, the PCV15 vaccine is a sterile liquid formulation of pneumococcal capsular polysaccharides of serotypes 3 conjugated to DTFB or DTFB C8 and pneumococcal capsular polysaccharides of serotypes 1, 4, 5, 6A, 6B, 7F, 9V, 14, 18C, 19A, 19F, 22F, 23F and 33F individually conjugated to $CRM_{197}$. Each 0.5 mL dose is formulated to contain: 2 µg of each saccharide, except for 6B at 4 µg; about 32 µg $CRM_{197}$ carrier protein (e.g., 32 µg±5 µg, ±3 µg, ±2 µg, or ±1 µg); about 2 µg DTFB or DTFB C8, 0.125 mg of elemental aluminum (0.5 mg aluminum phosphate) adjuvant; and sodium chloride and L-histidine buffer. The sodium chloride concentration is about 150 mM (e.g., 150 mM±25 mM, ±20 mM, ±15 mM, ±10 mM, or ±5 mM) and about 20 mM (e.g., 20 mM±5 mM, ±2.5 mM, ±2 mM, ±1 mM, or ±0.5 mM) L-histidine buffer.

In a particular embodiment of the present invention, the PCV15 vaccine is a sterile liquid formulation of pneumococcal capsular polysaccharides of serotypes 1, 3, 4, 5, 6A, 6B, 7F, 9V, 14, 18C, 19A, 19F, 22F, 23F and 33F individually conjugated to $CRM_{197}$. Each 0.5 mL dose is formulated to contain: 2 µg of each saccharide, except for 6B at 4 µg; about 32 µg $CRM_{197}$ carrier protein (e.g., 32 µg±5 µg, ±3 µg, ±2 µg, or ±1 µg), 0.125 mg of elemental aluminum (0.5 mg aluminum phosphate) adjuvant; and sodium chloride and L-histidine buffer. The sodium chloride concentration is about 150 mM (e.g., 150 mM±25 mM, ±20 mM, ±15 mM, ±10 mM, or ±5 mM) and about 20 mM (e.g., 20 mM±5 mM, ±2.5 mM, ±2 mM, ±1 mM, or ±0.5 mM) L-histidine buffer.

According to any of the methods of the present invention and in one embodiment, the subject is human. In certain embodiments, the human patient is an infant (less than 1 year of age), toddler (approximately 12 to 24 months), or young child (approximately 2 to 5 years). In other embodiments, the human patient is an elderly patient (>65 years). The compositions of this invention are also suitable for use with older children, adolescents and adults (e.g., aged 18 to 45 years or 18 to 65 years).

In one embodiment of the methods of the present invention, a composition of the present invention is administered as a single inoculation. In another embodiment, the vaccine is administered twice, three times or four times or more, adequately spaced apart. For example, the composition may be administered at 1, 2, 3, 4, 5, or 6 month intervals or any combination thereof. The immunization schedule can follow that designated for pneumococcal vaccines. For example, the routine schedule for infants and toddlers against invasive disease caused by S. pneumoniae is 2, 4, 6 and 12-15 months of age. Thus, in a preferred embodiment, the composition is administered as a 4-dose series at 2, 4, 6, and 12-15 months of age.

The compositions of this invention may also include one or more proteins from S. pneumoniae. Examples of S. pneumoniae proteins suitable for inclusion include those identified in International Patent Application Publication Nos. WO 02/083855 and WO 02/053761.

Formulations

The compositions of the invention can be administered to a subject by one or more method known to a person skilled in the art, such as parenterally, transmucosally, transdermally, intramuscularly, intravenously, intra-dermally, intranasally, subcutaneously, intra-peritonealy, and formulated accordingly.

In one embodiment, compositions of the present invention are administered via epidermal injection, intramuscular injection, intravenous, intra-arterial, subcutaneous injection, or intra-respiratory mucosal injection of a liquid preparation. Liquid formulations for injection include solutions and the like.

The composition of the invention can be formulated as single dose vials, multi-dose vials or as pre-filled syringes.

In another embodiment, compositions of the present invention are administered orally, and are thus formulated in a form suitable for oral administration, i.e., as a solid or a liquid preparation. Solid oral formulations include tablets, capsules, pills, granules, pellets and the like. Liquid oral formulations include solutions, suspensions, dispersions, emulsions, oils and the like.

Pharmaceutically acceptable carriers for liquid formulations are aqueous or non-aqueous solutions, suspensions, emulsions or oils. Examples of nonaqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs.

The pharmaceutical composition may be isotonic, hypotonic or hypertonic. However it is often preferred that a pharmaceutical composition for infusion or injection is essentially isotonic, when it is administrated. Hence, for storage the pharmaceutical composition may preferably be isotonic or hypertonic. If the pharmaceutical composition is hypertonic for storage, it may be diluted to become an isotonic solution prior to administration.

The isotonic agent may be an ionic isotonic agent such as a salt or a non-ionic isotonic agent such as a carbohydrate. Examples of ionic isotonic agents include but are not limited to NaCl, $CaCl_2$, KCl and $MgCl_2$. Examples of non-ionic isotonic agents include but are not limited to mannitol, sorbitol and glycerol.

It is also preferred that at least one pharmaceutically acceptable additive is a buffer. For some purposes, for example, when the pharmaceutical composition is meant for infusion or injection, it is often desirable that the composition comprises a buffer, which is capable of buffering a solution to a pH in the range of 4 to 10, such as 5 to 9, for example 6 to 8.

The buffer may for example be selected from the group consisting of Tris, acetate, glutamate, lactate, maleate, tartrate, phosphate, citrate, carbonate, glycinate, L-histidine, glycine, succinate and triethanolamine buffer.

The buffer may furthermore for example be selected from USP compatible buffers for parenteral use, in particular, when the pharmaceutical formulation is for parenteral use. For example the buffer may be selected from the group consisting of monobasic acids such as acetic, benzoic, gluconic, glyceric and lactic; dibasic acids such as aconitic, adipic, ascorbic, carbonic, glutamic, malic, succinic and tartaric, polybasic acids such as citric and phosphoric; and bases such as ammonia, diethanolamine, glycine, triethanolamine, and Tris.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, glycols such as propylene glycols or polyethylene glycol, Polysorbate 80 (PS-80), Polysorbate 20 (PS-20), and Poloxamer 188 (P188) are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

The formulations may also contain a surfactant. Preferred surfactants include, but are not limited to: the polyoxyethylene sorbitan esters surfactants (commonly referred to as the Tweens), especially PS-20 and PS-80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (TRITON™ X-100, or t-octylphenoxypolyethoxyethanol) being of particular interest; (octylphenoxy)polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. A preferred surfactant for including in the emulsion is PS-80.

Mixtures of surfactants can be used, e.g. PS-80/Span 85 mixtures. A combination of a polyoxyethylene sorbitan ester such as polyoxyethylene sorbitan monooleate (PS-80) and an octoxynol such as t-octylphenoxypolyethoxyethanol (TRITON™ X-100) is also suitable. Another useful combination comprises laureth 9 plus a polyoxyethylene sorbitan ester and/or an octoxynol.

Preferred amounts of surfactants are: polyoxyethylene sorbitan esters (such as PS-80) 0.01 to 1% w/v, in particular about 0.1% w/v; octyl- or nonylphenoxy polyoxyethanols (such as TRITON™ X-100, or other detergents in the Triton series) 0.001 to 0.1% w/v, in particular 0.005 to 0.02% w/v; polyoxyethylene ethers (such as laureth 9) 0.1 to 20% w/v, preferably 0.1 to 10% w/v and in particular 0.1 to 1% w/v or about 0.5% w/v.

In certain embodiments, the composition consists essentially of L-histidine (20 mM), saline (150 mM) and 0.2% w/v PS-20 at a pH of 5.8 with 250 ug/mL of APA (Aluminum Phosphate Adjuvant). PS-20 can range from 0.005 to 0.1% w/v with the presence of PS-20 or PS-80 in formulation controlling aggregation during simulated manufacture and in shipping using primary packaging. Process consists of combining blend of up to 44 serotypes in L-histidine, sodium chloride, and PS-20 then combining this blended material with APA and sodium chloride with or without antimicrobial preservatives.

As demonstrated herein, the choice of surfactant may need to be optimized for different drug products and drug substances. For multivalent vaccines containing 15 or more serotypes, PS-20 and P188 are preferred. The choice of chemistry used to prepare the conjugate can also influence the stabilization of the formulation. In particular, as exemplified below, pneumococcal polysaccharide-protein conjugates prepared in aqueous or DMSO solvent and combined in a multivalent composition show significant differences in stability depending on the particular surfactant systems used for formulation. As described, improved stability was observed with polysorbate 20 alone or with poloxamer 188 in combination with a polyol.

A poloxamer is a nonionic triblock copolymer composed of a central hydrophobic chain of polyoxypropylene (poly (propylene oxide)) flanked by two hydrophilic chains of polyoxyethylene (poly(ethylene oxide)). Poloxamers are also known by the tradename Pluronic®. Because the lengths of the polymer blocks can be customized, many different poloxamers exist that have slightly different properties. For the generic term "poloxamer", these copolymers are commonly named with the letter "P" (for poloxamer) followed by three digits, the first two digits×100 give the approximate molecular mass of the polyoxypropylene core, and the last digit×10 gives the percentage polyoxyethylene content (e.g., P407=Poloxamer with a polyoxypropylene molecular mass of 4,000 g/mol and a 70% polyoxyethylene content). For the Pluronic® tradename, coding of these copolymers starts with a letter to define its physical form at room temperature (L=liquid, P=paste, F=flake (solid)) followed by two or three digits. The first digit (two digits in a three-digit number) in the numerical designation, multiplied by 300, indicates the approximate molecular weight of the hydrophobe; and the last digit×10 gives the percentage polyoxyethylene content (e.g., L61=Pluronic® with a polyoxypropylene molecular mass of 1,800 g/mol and a 10% polyoxyethylene content). See U.S. Pat. No. 3,740,421.

Examples of poloxamers have the general formula:

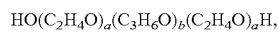

$$HO(C_2H_4O)_a(C_3H_6O)_b(C_2H_4O)_aH,$$

wherein a and b blocks have the following values:

| Pluronic® | Poloxamer | a | b | Molecular Weight |
|---|---|---|---|---|
| L31 | | 2 | 16 | 1100 (average) |
| L35 | | | | 1900 (average) |
| L44NF | 124 | 12 | 20 | 2090 to 2360 |
| L64 | | | | 2900 (average) |
| L81 | | | | 2800 (average) |
| L121 | | | | 4400 (average) |
| P123 | | 20 | 70 | 5750 (average) |
| F68NF | 188 | 80 | 27 | 7680 to 9510 |
| F87NF | 237 | 64 | 37 | 6840 to 8830 |
| F108NF | 338 | 141 | 44 | 12700 to 17400 |
| F127NF | 407 | 101 | 56 | 9840 to 14600 |

Molecular weight units, as used herein, are in Dalton (Da) or g/mol.

For the formulations described herein, a poloxamer generally has a molecular weight in the range from 1100 Da to 17,400 Da, from 7,500 Da to 15,000 Da, or from 7,500 Da to 10,000 Da. The poloxamer can be selected from poloxamer 188 or poloxamer 407. The final concentration of the poloxamer in the formulations of the invention is from 0.001 to 5% w/v, or 0.025 to 1% w/v. A surfactant system comprising a poloxamer must further comprise a polyol. In certain aspects, the polyol is propylene glycol and is at final concentration from 1 to 20% w/v. In certain aspects, the polyol is polyethylene glycol 400 and is at final concentration from 1 to 20% w/v.

Suitable polyols for the formulations are polymeric polyols, particularly polyether diols including, but are not limited to, propylene glycol and polyethylene glycol, Polyethylene glycol monomethyl ethers. Propylene glycol is available in a range of molecular weights of the monomer from ~425 to 2700. Polyethylene glycol and Polyethylene glycol monomethyl ether is also available in a range of molecular weights ranging from ~200 to 35000 including but not limited to PEG200, PEG300, PEG400, PEG1000 PEG MME 550, PEG MME 600, PEG MME 2000, PEG MME 3350 and PEG MME 4000. A preferred polyethylene glycol is polyethylene glycol 400. The final concentration of the polyol in the formulations may be 1 to 20% w/v or 6 to 20% w/v.

The formulation also contains a pH-buffered saline solution. The buffer may, for example, be selected from the group consisting of Tris, acetate, glutamate, lactate, maleate, tartrate, phosphate, citrate, carbonate, glycinate, L-histidine, glycine, succinate, HEPES (4-(2-hydroxyethyl)-1-piperazineethanesulfonic acid), MOPS (3-(N-morpholino)propanesulfonic acid), MES (2-(N-morpholino)ethanesulfonic acid) and triethanolamine buffer. The buffer is capable of buffering a solution to a pH in the range of 4 to 10, 5.2 to 7.5, or 5.8 to 7.0. In certain aspects, the buffer selected from the group consisting of phosphate, succinate, L-histidine, MES, MOPS, HEPES, acetate or citrate. The buffer may furthermore, for example, be selected from USP compatible buffers for parenteral use, in particular, when the pharmaceutical formulation is for parenteral use. The concentrations of buffer will range from 1 mM to 50 mM or 5 mM to 50 mM. In certain aspects, the buffer is L-histidine at a final concentration of 5 mM to 50 mM, or succinate at a final concentration of 1 mM to 10 mM. In certain aspects, the L-histidine is at a final concentration of 20 mM±2 mM.

While the saline solution (i.e., a solution containing NaCl) is preferred, other salts suitable for formulation include but are not limited to, $CaCl_2$, KCl and $MgCl_2$ and combinations thereof. Non-ionic isotonic agents including but not limited to sucrose, trehalose, mannitol, sorbitol and glycerol may be used in lieu of a salt. Suitable salt ranges include, but are not limited to 25 mM to 500 mM or 40 mM to 170 mM. In one aspect, the saline is NaCl, optionally present at a concentration from 20 mM to 170 mM.

In a preferred embodiment, the formulations comprise a L-histidine buffer with sodium chloride.

In certain embodiments of the formulations described herein, the polysaccharide-protein conjugates comprise one or more pneumococcal polysaccharides conjugated to a carrier protein. The carrier protein can be selected from $CRM_{197}$, diphtheria toxin fragment B (DTFB), DTFBC8, Diphtheria toxoid (DT), tetanus toxoid (TT), fragment C of TT, pertussis toxoid, cholera toxoid, *E. coli* LT, *E. coli* ST, exotoxin A from *Pseudomonas aeruginosa*, and combinations thereof. In certain aspects, one or more of the polysaccharide-protein conjugates are conjugated to DTFB. In one aspect, all of the polysaccharide-protein conjugates are prepared using aqueous chemistry. As an example, the polysaccharide-protein conjugate formulation can be a 15-valent pneumococcal conjugate (15vPnC) formulation consisting essentially of *S. pneumoniae* polysaccharide from serotypes 1, 4, 5, 6A, 6B, 7F, 9V, 14, 18C, 19A, 19F, 22F, 23 F and 33F conjugated to a $CRM_{197}$ polypeptide, and a *S. pneumoniae* polysaccharide from serotype 3 conjugated to a DTFB. In another aspect, one or more of the polysaccharide protein conjugates is prepared using DMSO chemistry. As an example, the polysaccharide-protein conjugate formulation can be a 15-valent pneumococcal conjugate (15vPnC) formulation wherein polysaccharide protein conjugates from serotypes 6A, 6B, 7F, 18C, 19A, 19F, and 23F are prepared using DMSO chemistry and polysaccharide protein conjugates from serotypes 1, 3, 4, 5, 9V, 14, 22F, and 33F are prepared using aqueous chemistry.

In another embodiment, the pharmaceutical composition is delivered in a controlled release system. For example, the agent can be administered using intravenous infusion, a transdermal patch, liposomes, or other modes of administration. In another embodiment, polymeric materials are used; e.g. in microspheres in or an implant.

The compositions of this invention may also include one or more proteins from *S. pneumoniae*. Examples of *S. pneumoniae* proteins suitable for inclusion include those identified in International Patent Application Publication Nos. WO 02/083855 and WO 02/053761.

Having described various embodiments of the invention with reference to the accompanying description and drawings, it is to be understood that the invention is not limited to those precise embodiments, and that various changes and modifications may be effected therein by one skilled in the art without departing from the scope or spirit of the invention as defined in the appended claims.

The following examples illustrate, but do not limit the invention.

EXAMPLES

Example 1: Preparation of DTFB Carrier Protein

Use of Multimodal Anion Exchange Chromatography for DTFB Preparation

Purified $CRM_{197}$, obtained through expression in *Pseudomonas fluorescens* as previously described (See International Patent Application Publication No. WO 2012/173876 A1), was digested with recombinant trypsin using a 1:500 molar ratio of trypsin to $CRM_{197}$ for approximately 1 hour at approximately 22° C. in 50 mM Tris, pH 8.0. Dithiothreitol (DTT) in 50 mM Tris, pH 8 was then added to a final concentration of 5 mM for 30 minutes at approximately 22° C. to reduce the disulfide bond between the A and B fragments of the proteolytically-cleaved $CRM_{197}$.

The digestion reaction was then loaded onto a multimodal anion exchange chromatography column (Capto™ Adhere, GE Healthcare) equilibrated with 50 mM Tris, pH 8. The column was washed with 50 mM Tris, pH 8, and the DTFB product was eluted with a gradient of 0.45 M to 0.65 M sodium chloride in 50 mM Tris, pH 8. The product was concentrated and diafiltered against 10 mM potassium phosphate, pH 8 using a 5 kDa Nominal Molecule Weight Cut-Off (NMWCO) tangential flow ultrafiltration membrane. The retentate containing DTFB product was 0.2-micron-filtered and stored at 2-8° C. Product concentration was determined by absorbance at 280 nm and purity was assessed by SDS-PAGE under non-reducing conditions.

Results show that the multimodal anion exchange chromatography eluent contained relatively pure DTFB, present primarily as a monomer with a small fraction of dimer. See FIG. 1A. Dimer formation was attributed to disulfide bond formation between DTFB monomers. As exemplified in the following sections, DTT has been used in the chromatography and ultrafiltration steps to minimize potential for dimer formation.

Use of Multimodal Cation Exchange Chromatography for DTFB Preparation

Due to the presence of DTFB dimers, an alternative purification method was investigated. Purified $CRM_{197}$, obtained through expression in *Pseudomonas fluorescens* as described above, was diluted to a protein concentration of approximately 1 mg/mL using 300 mM Tris, pH 7.5. Trypsin was added to the protein solution using a trypsin to $CRM_{197}$ molar ratio of approximately 1:3250. The solution was incubated for approximately 20 hours at room temperature. DTT in 300 mM Tris, pH 7.5 was then added to a final concentration of 10 mM DTT to reduce the disulfide bond between the proteolytically-cleaved $CRM_{197}$, separating the A and B fragments.

After approximately 75 minutes, the reduced protein solution was loaded onto a multimodal cation exchange chromatography column (Capto™ MMC, GE Healthcare). The column was equilibrated at 2-8° C. with 300 mM Tris, 10 mM DTT, pH 7.5 prior to loading the protein solution. After loading, the column was washed at 2-8° C. with 300 mM Tris, pH 7.5 containing 200 mM sodium chloride and 10 mM DTT, and the product was then eluted at 2-8° C. with 1 M sodium chloride in 300 mM Tris, pH 8.5. Approximately 0.002% w/v PS-20 was added to the batch prior to concentration at 2-8° C. using a 5 kDa NMWCO tangential flow ultrafiltration membrane. After concentration, additional PS-20 was added to the batch to a concentration of 0.02% w/v PS-20, and the batch was diafiltered against 100 mM potassium phosphate, 10 mM DTT, pH 8. The batch was further concentrated using tangential flow filtration with a 5 kDa membrane. The final retentate was 0.2-micron filtered and stored frozen or at 2-8° C. prior to conjugation.

Figure 1B:
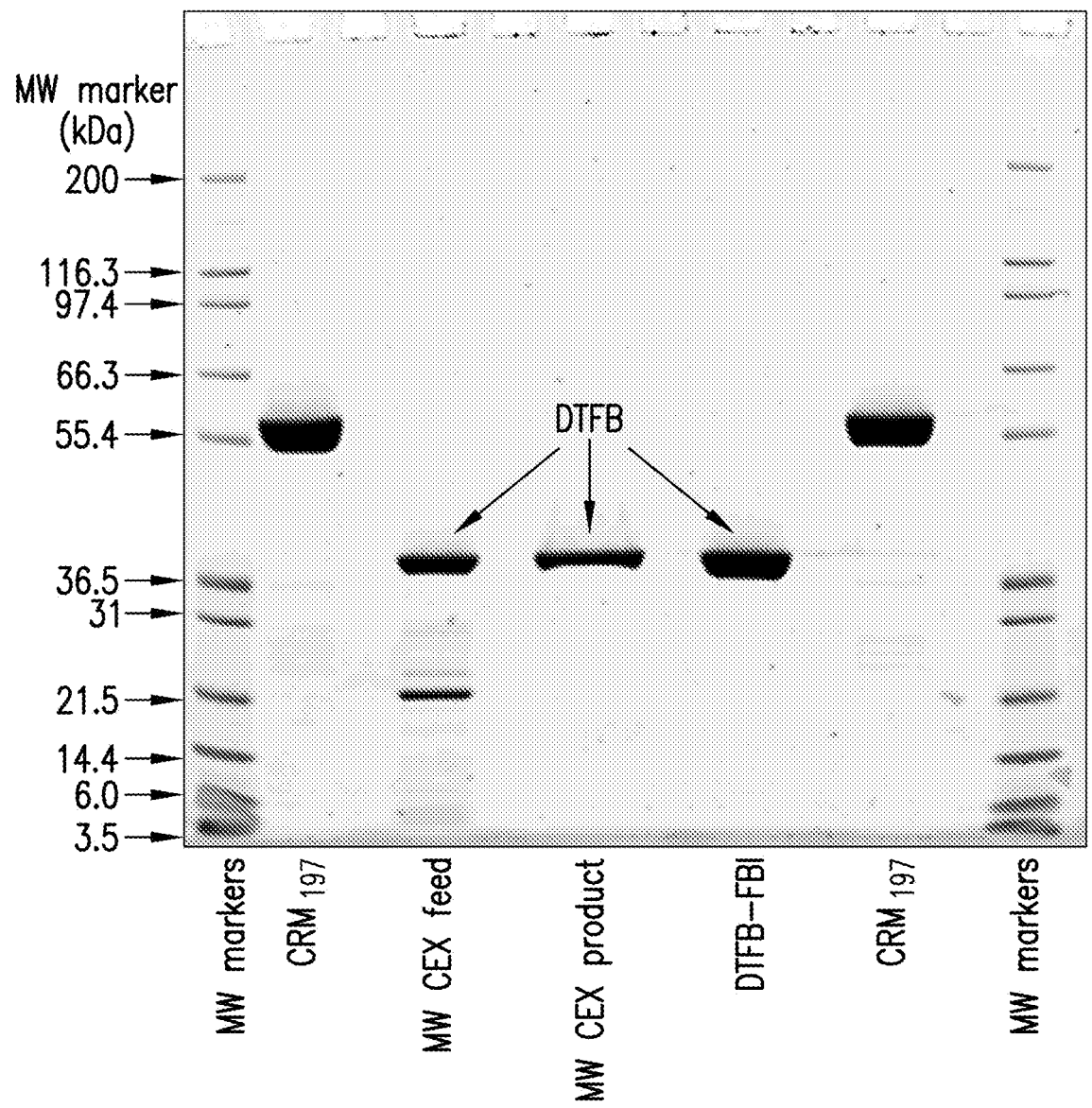
Figure 1C:
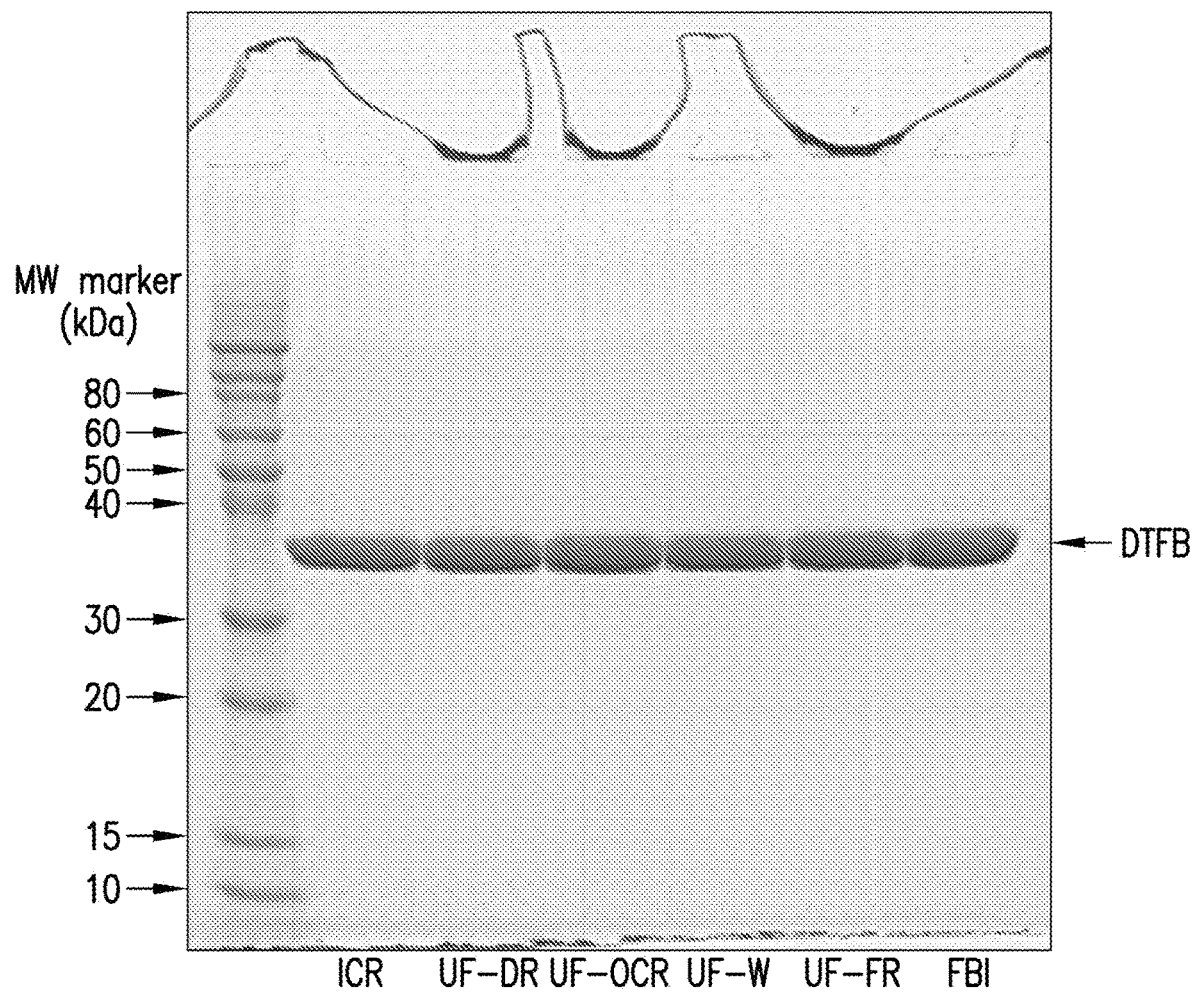

DTFB samples were analyzed by SDS-PAGE under reducing conditions (FIGS. 1B and 1C). Densitometric analysis of the gel shows that the final bulk intermediate after 0.2-micron filtration (FBI) has purity of >98%.

The final bulk intermediate (FBI) shown in FIG. 1C was analyzed by liquid chromatography with mass spectrometry (LC-MS) to measure intact protein mass. LC-MS analysis was performed on samples after reduction with DTT. Deconvolution of the raw data from the main peak resulted in a measured mass of 37,194.2 Da. This mass measurement is consistent with the theoretical mass of 37,194.4 Da for the DTFB, confirming the expected amino acid sequence.

A peptide map was obtained from a combination of trypsin, endoproteinase Asp-N, and endoproteinase Glu-C digestions. The sample was subjected to reductive alkylation with iodoacetamide in the presence of 6 M guanidine-HCl, and was digested for approximately 16-17 hours at 37° C. with each enzyme separately. The digestions were quenched by the addition of formic acid. Peptides were separated and analyzed by LC-MS. Using a combination of the peptides identified by the separate digestions, amino acid sequence coverage was approximately 98%. The peptides found were consistent with the predicted DTFB sequence.

Alternative Multimodal Cation Exchange Chromatography Process for DTFB Purification Purified $CRM_{197}$, obtained through expression in *Pseudomonas fluorescens* as described above, was diluted to a protein concentration of approximately 5 mg/mL using 300 mM Tris, pH 7.5. Trypsin was added to the protein solution using a trypsin to $CRM_{197}$ molar ratio of approximately 1:3000. The solution was incubated for approximately 15-20 hours at approximately 22° C. DTT in 300 mM Tris, pH 7.5 was then added to a final concentration of ≥10 mM DTT to reduce the disulfide bond between the proteolytically-cleaved $CRM_{197}$, separating the A and B fragments.

The reduced protein solution was loaded at onto a multimodal cation exchange chromatography column (Capto™ MMC, GE Healthcare) at approximately 25 g protein per L resin. The column was equilibrated at approximately 22° C. with 300 mM Tris, 10 mM DTT, pH 7.5 prior to loading the protein solution. After loading, the column was washed at approximately 22° C. with 300 mM Tris, pH 7.5 containing 200 mM sodium chloride and 10 mM DTT, and the product was then eluted at 22° C. with 1 M sodium chloride in 300 mM Tris, pH 8.5. DTFB product from the multimodal cation exchange chromatography can be diafiltered and concentrated using a 5 kDa NMWCO tangential flow ultrafiltration membrane and 0.2-micron filtered as described above.

Figure 1D:
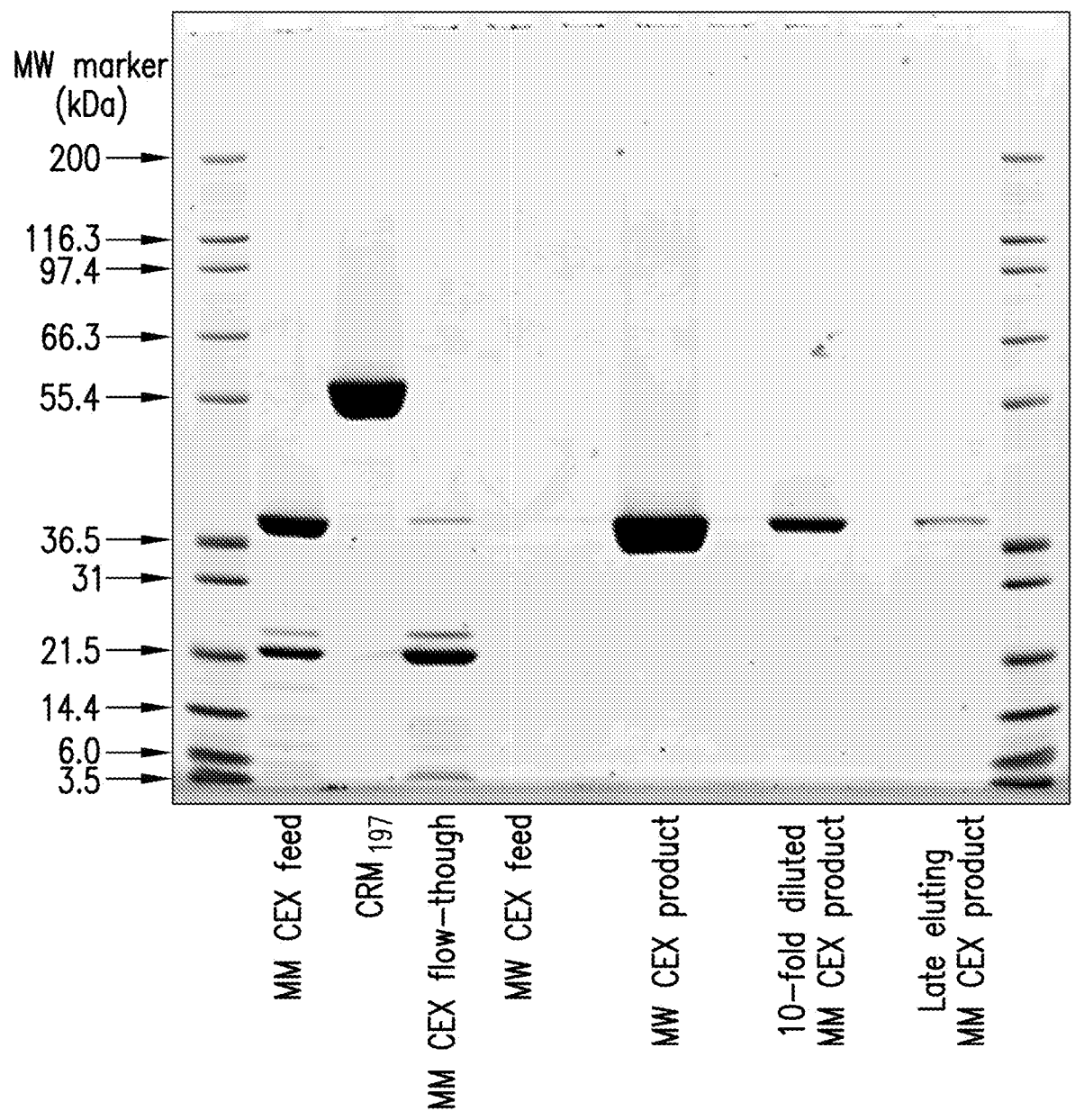

DTFB samples from the multimodal cation exchange process were analyzed by SDS-PAGE under reducing conditions (FIG. 1D). Densitometric analysis of the gel shows that the DTFB protein product eluted from the multimodal cation exchange column is highly purified.

Effects of Buffer pH, Ionic Strength, and PS-20 Surfactant Concentration on DTFB Stability During Ultrafiltration Buffer pH, ionic strength and PS-20 surfactant studies were conducted to address protein particle formation observed during development of the DTFB ultrafiltration step. DTFB was adjusted to 100 mM potassium phosphate at pH 7, 7.5, or pH 8 with 0, 200, or 500 mM sodium chloride. Differential scanning calorimetry was used to assess the stability (melting temperature, Tm) of the DTFB solutions as function of pH and sodium chloride concentration. As shown in Table 1, increasing the pH from 7 to 8 increased the DTFB Tm by approximately 3° C. Sodium chloride in the range of 0 to 500 mM sodium chloride did not significantly impact Tm at the pH values investigated.

TABLE 1

Stability of DTFB solutions as a function of buffer pH and sodium chloride concentration as measured by differential scanning calorimetry

| pH of potassium phosphate buffer | Sodium chloride concentration (mM) | Melting temperature, Tm (° C.) |
|---|---|---|
| 7 | 0 | 50.6 |
|  | 200 | 50.4 |
|  | 500 | 50.6 |
| 7.5 | 0 | 51.5 |
|  | 200 | 51.3 |
|  | 500 | 51.2 |
| 8 | 0 | 52.8 |
|  | 200 | 53.2 |
|  | 500 | 53.3 |

In a separate study, purified DTFB was adjusted to pH 6.0, pH 7.0, and pH 8.5 in 100 mM potassium phosphate with 0, 150, 500, and 1000 mM sodium chloride. Solutions were held overnight at room temperature and then centrifuged to remove precipitated protein. Supernatants were assayed for protein concentration by size exclusion chromatography with UV280 absorbance detection (FIG. 2). Supernatant protein concentration in this study was not affected by solution pH at 0 and 150 mM sodium chloride. However, at higher sodium chloride concentrations (500 and 1000 mM), results show a pronounced decrease in supernatant protein concentration, indicative of reduced DTFB stability, as buffer pH decreased from pH 7.0 or 8.5 to 6.0.

The effect of PS-20 concentration on DTFB stability was studied by adding increasing amounts of PS-20 to DTFB solutions in 50 and 100 mM potassium phosphate, pH 8 solutions and in 50 mM potassium phosphate, 150 mM sodium chloride, pH 8. Solutions were vortexed for 5 minutes and then centrifuged. Supernatants were assayed for protein concentration by size exclusion chromatography with UV280 absorbance detection (FIG. 3). Significant vortex-induced protein loss was observed in samples containing no PS-20. DTFB recovery was notably improved in samples containing ≥0.01% w/v PS-20.

Example 2: Preparation of *S. pneumoniae* Capsular Polysaccharides

Methods of culturing pneumococci are well known in the art. See, e.g., Chase, 1967, *Methods of Immunology and Immunochemistry* 1:52. Methods of preparing pneumococcal capsular polysaccharides are also well known in the art. See, e.g., European Patent No. EP0497524. Isolates of pneumococcal subtypes are available from the American Type Culture Collection (Manassas, Va.). The bacteria are identified as encapsulated, non-motile, Gram-positive, lancet-shaped diplococci that are alpha-hemolytic on blood-agar. Subtypes can be differentiated on the basis of Quelling reaction using specific antisera. See, e.g., U.S. Pat. No. 5,847,112.

Cell banks representing each of the *S. pneumoniae* serotypes of interest were obtained from the Merck Culture Collection (Rahway, N.J.) in a frozen vial. A thawed seed culture was transferred to the seed fermentor containing a pre-sterilized growth media appropriate for *S. pneumoniae*. The culture was grown in the seed fermentor with temperature and pH control. The entire volume of the seed fermentor was transferred to a production fermentor containing presterilized growth media. The production fermentation was the final cell growth stage of the process. Temperature, pH, and the agitation rate were controlled.

The fermentation process was terminated via the addition of an inactivating agent. After inactivation, the batch was transferred to the inactivation tank where it was held at controlled temperature and agitation. Cell debris was removed using a combination of centrifugation and filtration. The batch was ultrafiltered and diafiltered. The batch was then subjected to solvent-based fractionations that remove impurities and recover polysaccharide.

Example 3: Conjugation of Polysaccharides to DTFB Carrier Protein Using Reductive Amination in Aqueous Solution Preparation of Serotype 3-DTFB (ST3-DTFB) Conjugate for Mouse Immunogenicity Studies Purified serotype 3 polysaccharide obtained as described in Example 2 was dissolved in water. Ps size reduction to an average molecular weight of approximately 200 kDa was performed using a probe sonicator with the sample cooled in ice. The sonicated sample was 0.2 micron-filtered and stored at 2-8° C. The polysaccharide solution was concentrated by diafiltration against a 30 kDa NMWCO tangential flow filtration membrane.

Polysaccharide was prepared for conjugation using sodium metaperiodate oxidation (See Anderson et al., 1986, *J Immunol*. 137:1181-1186; and U.S. Patent Application Publication No. US20110195086). A 100 mM sodium metaperiodate solution was added to the polysaccharide solution in 50 mM sodium acetate. The sample was mixed for 14-18 hours at 19-25° C. protected from light. Ethylene glycol (100:1 molar excess over polysaccharide repeat units) was added and mixed an additional 16-18 hours at 19-25° C. to quench residual sodium metaperiodate and stop the oxidation reaction. The resulting solution was diafiltered against 10 volumes of water. The oxidized polysaccharide solution was stored in aliquots at −70° C.

The periodate-oxidized polysaccharide was mixed with DTFB prepared as described in Example 1 (using multi-modal anion exchange chromatography) at a polysaccharide to protein mass ratio of 0.6:1. Potassium phosphate, pH 6.4 and nickel chloride were added to final concentrations of 145 mM and 2.2 mM, respectively. Sodium cyanoborohydride to approximately 1-2 molar equivalents was then added. The reaction was protected from light and carried out over a period of 120 hours at 2-8° C.

The mixture was then dialyzed against 2 changes of 25 mM potassium phosphate buffer, pH 6.4, 0.3 M sodium chloride at 2-8° C. for a total of 14-18 hours. Insoluble materials were removed by brief centrifugation, and the conjugate was polished by size exclusion chromatography (SEC) to reduce free polysaccharide and protein. The SEC-polished conjugate was concentrated over a 30 kD NMWCO centrifugal concentrator.

Preparation of Serotype 3-DTFB Conjugate for Infant Rhesus Monkey Immunogenicity Study Purified Serotype 3 pneumococcal capsular polysaccharide powder was dissolved in water and 0.45-micron filtered. The batch was homogenized to reduce the molecular mass of the Ps and 0.22-micron filtered. Size reduction of *Streptococcus pneumoniae* polysaccharide, prior to conjugation, has been described previously as means to generate polysaccharide with more specific, reproducible, and manageable physical properties (Marburg et al., 1997, U.S. Pat. No. 5,623,057). As described by Marburg et al., polysaccharide size reduction is known to increase solubility and filterability and to reduce polydispersity and viscosity, thereby improving conjugation consistency and ease of conjugation. Polysaccharide size reduction of serotype 19F polysaccharide from *Streptococcus pneumoniae* using homogenization has been described previously (Lander et al., 2000, *Biotechnol. Prog.* 2000, 16, 80-85). The size-reduced polysaccharide was then concentrated and diafiltered against water using a 10 kDa NMWCO tangential flow ultrafiltration membrane.

50 mM sodium acetate was then added, and polysaccharide activation was initiated with the addition of a 100 mM sodium metaperiodate solution to form reactive aldehydes on the polysaccharide. The batch was incubated at approximately 22° C. for approximately 12 hours. The batch was diafiltered against 10 mM potassium phosphate, pH 6.4 using a 10 kDa NMWCO tangential flow ultrafiltration membrane at ≤8° C. and the product-rich retentate was concentrated.

Activated polysaccharide solution was blended with water and 1.5 M potassium phosphate, pH 7.0. Purified DTFB was 0.2-micron filtered, and then combined with the buffer-adjusted polysaccharide solution at a polysaccharide to protein mass ratio of 1.3:1. The solution was then 0.2 micron filtered. Nickel chloride was added to the batch to a final concentration of approximately 2 mM using a 100 mM nickel chloride stock solution. Sodium cyanoborohydride (2 moles per mole of polysaccharide repeating unit) was then added. The batch was allowed to react for approximately 120 hours at approximately 10° C. to maximize consumption of polysaccharide and protein.

Following the conjugation reaction, the batch was diluted to a polysaccharide concentration of approximately 3.5 g/L, cooled to 2-8° C., 1.2 micron filtered, and diafiltered against 100 mM potassium phosphate, pH 7.0 at 2-8° C. using a 100 kDa NMWCO tangential flow ultrafiltration membrane. The batch, recovered in the retentate, was then diluted to approximately 2.0 g polysacharude/L and pH-adjusted with the addition of 1.2 M sodium bicarbonate, pH 9.4. Sodium borohydride (1 mole per mole of polysaccharide repeating unit) was added. 1.5 M potassium phosphate, pH 6.0 was later added.

The batch was then concentrated and diafiltered against 10 mM L-histidine in 150 mM sodium chloride, pH 7.0 at 2-8° C. using a 300 kDa NMWCO tangential flow ultrafiltration membrane. The retentate was 0.2 micron filtered and adjusted to a polysaccharide concentration of 1.0 g/L with additional 10 mM L-histidine in 150 mM sodium chloride, pH 7.0. The batch was dispensed into aliquots and frozen at ≤−60° C.

Example 4: Conjugation of Serotypes 1, 3, 4, 5, 6A, 6B, 7F, 9V, 14, 18C, 19A, 19F, 22F, 23F, and 33F to $CRM_{197}$ Using Reductive Amination in Aqueous Solution The different serotype polysaccharides were individually conjugated to purified $CRM_{197}$ carrier protein using a common process flow. Polysaccharide was dissolved, size reduced, chemically activated and buffer-exchanged by ultrafiltration. Purified $CRM_{197}$ was then conjugated to the activated polysaccharide utilizing $NiCl_2$ (2 mM) in the reaction mixture, and the resulting conjugate was purified by ultrafiltration prior to a final 0.2 micron filtration. Several process parameters within each step, such as pH, temperature, concentration, and time were controlled to serotype-specific values in section below.

Polysaccharide Size Reduction and Oxidation

Purified pneumococcal capsular polysaccharide powder was dissolved in water, and all serotypes, except serotype 19A, were 0.45-micron filtered. Serotypes 1, 3, 4, 5, 6A, 6B, 7F, 9V, 14, 19A, 19F, 22F, 23F, and 33F were homogenized to reduce the molecular mass of the polysaccharide. Serotype 18C was size-reduced by either homogenization or acid hydrolysis at ≥90° C. Serotype 19A was not size reduced due to its relatively low starting size. Homogenization pressure and number of passes through the homogenizer were controlled to serotype-specific targets (150-1000 bar; 4-7 passes) to achieve a serotype-specific molecular mass. Size-reduced polysaccharide was 0.2-micron filtered and then concentrated and diafiltered against water using a 10 kDa NMWCO tangential flow ultrafiltration membrane. A 5 kDa NMWCO membrane was used for acid-hydrolyzed serotype 18C.

The polysaccharide solution was then adjusted to a serotype-specific temperature (4-22° C.) and pH (4-5) with a sodium acetate buffer to minimize polysaccharide size reduction due to activation. For all serotypes (except serotype 4), polysaccharide activation was initiated with the addition of a 100 mM sodium metaperiodate solution. The amount of sodium metaperiodate added was serotype-specific, ranging from approximately 0.1 to 0.5 moles of sodium metaperiodate per mole of polysaccharide repeating unit. The serotype-specific charge of sodium metaperiodate was to achieve a target level of polysaccharide activation (moles aldehyde per mole of polysaccharide repeating unit). For serotype 4, prior to the sodium metaperiodate addition, the batch was incubated at approximately 50° C. and pH 4.1 to partially deketalize the polysaccharide.

For all serotypes, with the exception of serotypes 5 and 7F, the activated product was diafiltered against 10 mM potassium phosphate, pH 6.4 using a 10 kDa NMWCO tangential flow ultrafiltration membrane. A 5 kDa NMWCO membrane was used for acid-hydrolyzed serotype 18C.

Serotypes 5 and 7F were diafiltered against 10 mM sodium acetate. Ultrafiltration for all serotypes was conducted at 2-8° C.

Polysaccharide Conjugation to $CRM_{197}$

Oxidized polysaccharide solution was mixed with water and 1.5 M potassium phosphate, pH 6.0 or pH 7.0, depending on the serotype. The buffer pH selected was to improve the stability of activated polysaccharide during the conjugation reaction. Purified $CRM_{197}$, obtained through expression in *Pseudomonas fluorescens* as previously described (WO 2012/173876 A1), was 0.2-micron filtered and combined with the buffered polysaccharide solution at a polysaccharide to $CRM_{197}$ mass ratio ranging from 0.4 to 1.0 w/w depending on the serotype. The mass ratio was selected to control the polysaccharide to $CRM_{197}$ ratio in the resulting conjugate. The polysaccharide and phosphate concentrations were serotype-specific, ranging from 3.6 to 10.0 g/L and 100 to 150 mM, respectively, depending on the serotype. The serotype-specific polysaccharide concentration was selected to control the size of the resulting conjugate. The solution was then 0.2-micron filtered. Nickel chloride was added to approximately 2 mM using a 100 mM nickel chloride solution. Sodium cyanoborohydride (2 moles per mole of polysaccharide repeating unit) was added. Conjugation proceeded for a serotype-specific duration (72 to 120 hours) to maximize consumption of polysaccharide and protein.

Acid-hydrolyzed serotype 18C was conjugated at 37° C. in 100 mM potassium phosphate at approximately pH 8 with sodium cyanoborohydride using polysaccharide and protein concentrations of approximately 12.0 g/L and 6.0 g/L, respectively.

Reduction with Sodium Borohydride

Following the conjugation reaction, the batch was diluted to a polysaccharide concentration of approximately 3.5 g/L, cooled to 2-8° C., and 1.2-micron filtered. All serotypes (except serotype 5) were diafiltered against 100 mM potassium phosphate, pH 7.0 at 2-8° C. using a 100 kDa NMWCO tangential flow ultrafiltration membrane. The batch, recovered in the retentate, was then diluted to approximately 2.0 g polysaccharide/L and pH-adjusted with the addition of 1.2 M sodium bicarbonate, pH 9.4. Sodium borohydride (1 mole per mole of polysaccharide repeating unit) was added. 1.5 M potassium phosphate, pH 6.0 was later added. Serotype 5 was diafiltered against 300 mM potassium phosphate using a 100 kDa NMWCO tangential flow ultrafiltration membrane.

Final Filtration and Product Storage

The batch was then concentrated and diaftiltered against 10 mM L-histidine in 150 mM sodium chloride, pH 7.0 at 4° C. using a 300 kDa NMWCO tangential flow ultrafiltration membrane. The retentate batch was 0.2 micron filtered.

Serotype 19F was incubated for approximately 7 days at 22° C., diafiltered against 10 mM L-histidine in 150 mM sodium chloride, pH 7.0 at 4° C. using a 100 kDa NMWCO tangential flow ultrafiltration membrane, and 0.2-micron filtered.

The batch was adjusted to a polysaccharide concentration of 1.0 g/L with additional 10 mM L-histidine in 150 mM sodium chloride, pH 7.0. The batch was dispensed into aliquots and frozen at ≤−60° C.

Example 5: Methods for the Conjugation of Serotypes 6A, 6B, 7F, 18C, 19A, 19F, and 23F to $CRM_{197}$ Using Reductive Amination in Dimethylsulfoxide The different serotype polysaccharides were individually conjugated to purified $CRM_{197}$ carrier protein using a common process flow. Polysaccharide was dissolved, sized to a target molecular mass, chemically activated and buffer-exchanged by ultrafiltration. Activated polysaccharide and purified $CRM_{197}$ were individually lyophilized and redissolved in dimethylsulfoxide (DMSO). Redissolved polysaccharide and $CRM_{197}$ solutions were then combined and conjugated as described below. The resulting conjugate was purified by ultrafiltration prior to a final 0.2-micron filtration. Several process parameters within each step, such as pH, temperature, concentration, and time were controlled to serotype-specific values in section below.

Polysaccharide Size Reduction and Oxidation

Purified pneumococcal capsular polysaccharide powder was dissolved in water, and all serotypes, except serotype 19A, were 0.45-micron filtered. All serotypes, except serotypes 18C and 19A, were homogenized to reduce the molecular mass of the polysaccharide. Homogenization pressure and number of passes through the homogenizer were controlled to serotype-specific targets (150-1000 bar; 4-7 passes). Serotype 18C was size-reduced by acid hydrolysis at ≥90° C. Serotype 19A was not sized-reduced.

Size-reduced polysaccharide was 0.2-micron filtered and then concentrated and diafiltered against water using a 10 kDa NMWCO tangential flow ultrafiltration membrane. A 5 kDa NMWCO membrane was used for serotype 18C.

The polysaccharide solution was then adjusted to a serotype-specific temperature (4-22° C.) and pH (4-5) with a sodium acetate buffer. Polysaccharide activation was initiated with the addition of a sodium metaperiodate solution. The amount of sodium metaperiodate added was serotype-specific, ranging from approximately 0.1 to 0.5 moles of sodium metaperiodate per mole of polysaccharide repeating unit.

For all serotypes, the activated product was diafiltered against 10 mM potassium phosphate, pH 6.4 using a 10 kDa NMWCO tangential flow ultrafiltration membrane. A 5 kDa NMWCO membrane was used for serotype 18C. Ultrafiltration for all serotypes was conducted at 2-8° C.

Polysaccharide Conjugation to $CRM_{197}$

Purified $CRM_{197}$, obtained through expression in *Pseudomonas fluorescens* as previously described (WO 2012/173876 A1), was diafiltered against 2 mM phosphate, pH 7 buffer using a 5 kDa NMWCO tangential flow ultrafiltration membrane and 0.2-micron filtered.

The oxidized polysaccharide solution was formulated with water and sucrose in preparation for lyophilization. The protein solution was formulated with water, phosphate buffer, and sucrose in preparation for lyophilization. Sucrose concentrations ranged from 1 to 5% to achieve optimal redissolution in DMSO following lyophilization.

Formulated polysaccharide and $CRM_{197}$ solutions were individually lyophilized. Lyophilized polysaccharide and $CRM_{197}$ materials were redissolved in DMSO and combined using a tee mixer. Sodium cyanoborohydride (1 mole per mole of polysaccharide repeating unit) was added, and conjugation proceeded for a serotype-specific duration (1 to 48 hours) to achieve a targeted conjugate size.

Reduction with Sodium Borohydride

Sodium borohydride (2 mole per mole of polysaccharide repeating unit) was added following the conjugation reaction. The batch was diluted into 150 mM sodium chloride at approximately 4° C. Potassium phosphate buffer was then added to neutralize the pH. The batch was concentrated and diafiltered at approximately 4° C. against 150 mM sodium chloride using a 10 kDa NMWCO tangential flow ultrafiltration membrane.

Final Filtration and Product Storage

Each batch was then concentrated and diafiltered against 10 mM L-histidine in 150 mM sodium chloride, pH 7.0 at 4° C. using a 300 kDa NMWCO tangential flow ultrafiltration membrane. The retentate batch was 0.2-micron filtered.

Serotype 19F was incubated for approximately 5 days, diafiltered against 10 mM L-histidine in 150 mM sodium chloride, pH 7.0 at approximately 4° C. using a 300 kDa NMWCO tangential flow ultrafiltration membrane, and 0.2-micron filtered.

The batch was diluted with additional 10 mM L-histidine in 150 mM sodium chloride, pH 7.0 and dispensed into aliquots and frozen at ≤−60° C.

Example 6: Mouse Immunogenicity Study Using ST3-DTFB Monovalent Conjugate Formulation The immungenicity of ST3-DTFB compared to ST3-$CRM_{197}$ was evaluated in a mouse model. Adjuvanted formulations for administration to mice were prepared by mixing 24 µL of sterile-filtered conjugate (1:10 in saline—0.1258 mg DTFB or $CRM_{197}$-conjugated polysaccharide per mL) with 62 µL of APA, and 3.664 ml of sterile saline for a dose of 0.08 µg of polysaccharide and 5 µg of aluminum per 100 µL. The formulated vaccines were stored in individual borosilicate stoppered vials at 2-8° C. to support individual immunizations.

ST3-DTFB was evaluated in 6-8 week old female Balb/C mice (n=10/group). Mice were immunized with ST3-DTFB/APA and two ST3-$CRM_{197}$/APA lots made using unique ST3-DTFB and ST3-$CRM_{197}$ conjugate preparations prepared as described in Examples 3 and 4. The ST3 PnPs concentration was 0.08 µg per dose in a 0.1 ml volume, with 5 µg of APA, given intraperitoneally on days 0, 14 and 28. Sera were collected prior to study start (pre) and on day 39, post-dose 3 (PD3) and tested in a ST3 WHO ELISA [per standardized World Health Organization (WHO) protocols] as well as in a protein carrier ELISA ($CRM_{197}$ and DTFB). Mice were challenged intraperitoneally with *S. pneumoniae* serotype 3 (207 CFU/0.5 ml) on day 49.

WHO ELISA results (FIG. 4) showed mice immunized with both ST3-DTFB/APA and ST3-$CRM_{197}$/APA had similar PD3 PnPs 3 titers. Mice immunized with ST3-DTFB/APA and ST3-$CRM_{197}$/APA had ≥90% protection against a serotype 3 challenge, which was significantly higher relative to the negative control saline and APA immunized mice (FIG. 5).

Example 7: Formulation of a 15-Valent Pneumococcal Conjugate Vaccine with Different Surfactants and Stabilizers Pneumococcal polysaccharide-protein conjugates prepared as described above were used for the formulation of a 15-valent pneumococcal conjugate vaccine (PCV15) having serotypes 1, 3, 4, 5, 6A, 6B, 7F, 9V, 14, 18C, 19A, 19F, 22F, 23F, and 33F. The formulations were prepared using pneumococcal polysaccharide-$CRM_{197}$ conjugates generated by reductive amination in aqueous solutions (Example 4) or in DMSO (Example 5). ST3-DTFB conjugates were prepared as per Example 3. The required volumes of bulk conjugates needed to obtain the target concentration of individual serotypes were calculated based on the batch volume and the bulk polysaccharide concentrations. The 15 conjugates were combined with the excipients selected from sodium chloride, L-histidine, pH 5.8 buffer with PS-20, PS-80, or P188.

The sterile formulated bulk was mixed gently during and following its blending with bulk Aluminum Phosphate Adjuvant (APA) with or without propylene glycol (PG) and polyethylene glycol 400 (PEG400). Two concentrations of conjugates and APA were studied in the various formulations. One contained 8 µg/mL serotype 6B polysaccharide, 4 µg/mL polysaccharide for all other serotypes, and 250 µg/mL APA. The other contained 16 µg/mL serotype 6B polysaccharide, 8 µg/mL polysaccharide for all other serotypes, and 500 µg/mL APA. The formulated vaccines were stored at 2-8° C.

Example 8: Impact of Excipients on Stability of a Pneumococcal Conjugate Vaccine Formulation Containing Conjugates Generated by Reductive Amination in Aqueous Solution The stability of a 15-valent Pneumococcal Conjugate Vaccine (PCV15), prepared as described in Example 7, was evaluated for various excipient conditions after stirring, recirculation, and rotational agitation studies to simulate manufacturing and shipping stresses that could occur. PCV15 was prepared with 20 mM L-histidine, pH 5.8, 150 mM sodium chloride, and either one of the two concentrations of conjugates and APA listed in Example 7. Since results were very similar between the two formulations at different concentrations of conjugates and APA, only results for the PCV15 formulation containing lower concentrations of conjugates and APA were shown in this Example. For the stirring studies, the PCV15 formulations were mixed using a magenetic stir bar in a glass vessel. For recirculation and shear studies, the PCV15 formulations were recirculated in a tubing loop. For the rotational studies, the PCV15 base formulation (L-histidine, pH 5.8 and sodium chloride) was prepared and surfactants or stabilizers were added as outlined in Example 7 and Table 2. The agitation studies were designed using rotational side agitation for up 24 hours at 4° C. Visual assessment was used to evaluate the formulations. A path of a beam of light passing through the vessel allowed for the detection of particulates. Furthermore, the impact of manufacturing and shipping and handling stresses on particle size distribution was evaluated using static light scattering (SLS). Static light scattering of a suspension based drug product allows for the more sensitive detection of aggregation as indicated by particle size distribution. A monodisperse (monomodal) particle size distribution of a PCV15 drug product is indicative of a non-aggregated drug product. However a polydisperse, polymodal particle size distribution is indicative of aggregation.

Stability of PCV15 in the Stirring Study

PCV15 formulations utilizing pneumococcal polysaccharide drug substances conjugated using reductive amination under aqueous conditions to $CRM_{197}$ (referred to as $PCV15_{Aq}$), as described in Example 4, were screened using laboratory scale mixing experimental setup, as above (beaker and magnetic stir bar). $PCV15_{Aq}$ contains polysaccharide from S. pneumoniae serotypes 1, 3, 4, 5, 6A, 6B, 7F, 9V, 14, 18C, 19A, 19F, 22F, 23F and 33F conjugated to $CRM_{197}$ using reductive amination under aqueous conditions. PCV15 in 20 mM L-histidine, 150 mM NaCl with APA was prepared in a 100 mL laboratory scale batch using a beaker and magenetic stir bar. In the absence of a surfactant, the $PCV15_{Aq}$ formulations were prone to manufacture (stirring) induced damage resulting in aggregation of the vaccine drug product during stirring to ensure homogeneity of the vaccine drug product.

A class of non-ionic triblock copolymers were found to provide robust stability during screening studies of various excipients. Poloxamer 188 (P188) was selected to control aggregation and provide a robust and stable vaccine drug product formulation. $PCV15_{Aq}$ formulations were prepared with 20 mM L-histidine, pH 5.8, 150 mM NaCl, APA, and either no P188, 0.08% w/v P188, or 0.24% w/v P188. The impact of time under constant stirring using a magnetic stir bar was evaluated using static light scattering (FIGS. 6-7). Particle size distribution was assessed using a Malvern Mastesizer 2000. A 5 µm NIST particle size standard was run and produced the expected size distribution. For all formulations (with and without Poloxamer 188), a monodisperse histogram profile was observed following addition of the conjugates to APA (T=0 hr Stirring). In as little as 7 hours (T=7 hr Stirring) of continuous mixing, the formulation without P188 resulted in the appearance of increased particle size distribution and aggregation (FIG. 6). However, formulations containing P188 at either concentration showed no appearance of increased particle size or aggregation upon continuous mixing up to 24 hours (T=24 hr Stirring) (FIG. 7).

Stability of PCV15 in the Horizontal Agitation Study

Additional $PCV15_{Aq}$ formulations in 20 mM L-histidine, pH 5.8, 150 mM NaCl, and APA and with or without 0.2% w/v P188 were prepared in a 100 mL laboratory scale batch preparation as described in Example 7. To simulate shipping and handling and evaluate the impact to stability of the vaccine drug product, a horizontal agitation study was utilized. The study represents a direct agitation of the $PCV15_{Aq}$ formulation through interactions with the surfaces in a container closure system (syringe or vial) and exposure of the formulation to final container components and an air interface. 0.64 mL was dispensed into syringes and stoppered. These syringes were horizontally rotated at 2-8° C. for 24 hours and evaluated for particle size distribution using SLS (FIG. 8A). A visual assessment was also performed (FIG. 8B). The $PCV15_{Aq}$ formulation in the absence of P188 and subjected to simulated shipping and handling stresses results in an increase in particle size distribution of the drug product and visible signs of agglomeration and aggregation with a container closure system such as a syringe. The PCV15 formulation with P188 did not show an increase in particle size distribution or visual signs of agglomeration and aggregation.

Example 9: Impact of Excipients on Stabilizing a Pneumococcal Conjugate Vaccine Drug Product Prepared Using a Mixture Conjugates Generated by Reductive Aminatinon in Aqueous and DMSO Solutions Multiple 15-valent (PCV15) formulations with APA in 20 mM L-histidine, pH 5.8, 150 mM NaCl were evaluated using laboratory scale simulated shipping studies to ensure a robust manufacturable and commercially viable vaccine drug product formulation. Formulation $PCV15_{Aq}$ contained pneumococcal polysaccharide-$CRM_{197}$ conjugates generated by reductive amination in aqueous solution. Formulation $PCV15_{Aq/Non-Aq}$ contained serotype 6A, 6B, 7F, 19A, 19F, and 23F conjugates prepared using reductive amination in DMSO and serotype 1, 3, 4, 5, 9V, 14, 18C, 22F, and 33F conjugates prepared using reductive amination in aqueous solution, where all polysaccharides were conjugated to $CRM_{197}$. Formulation $PCV15_{Aq/Non-Aq/ST3-DTFB}$ was similar to $PCV15_{Aq/Non-Aq}$ except that serotype 3 was conjugated to DTFB protein, not $CRM_{197}$. Since the results were very similar between the two formulations at different concentrations of conjugates and APA listed in Example 7, only results for PCV15 formulation containing lower concentrations of conjugates and APA were shown in this example, unless otherwise specified.

To evaluate the impact to stability of the vaccine formulations, a horizontal agitation study was utilized. The study represents a direct agitation of formulations through interactions with the surfaces in a container closure system (syringe or vial) and exposure of the formulation to final container components and an air interface. Formulations were dispensed as 0.64 mL fill into syringes and stoppered. These syringes were horizontally rotated at 2-8° C. for up to 8 hr. The impact of time under horizontal agitation was evaluated for particle size distribution using static light scattering (SLS). Particle size and distribution were assessed using a Malvern Mastesizer 2000. A 5 μm NIST particle size standard was run and produced expected size distribution. As shown in FIG. 9, P188 was not an effective stabilizer for controlling aggregation for the PCV15$_{Aq/Non-Aq/ST3-DTFB}$ formulation despite being a robust stabilizer for the PCV15$_{Aq}$ formulation. An increase in particle size distribution and visible signs of agglomeration and aggregation were noted in the PCV15$_{Aq/Non-Aq/ST3-DTFB}$ formulation with P188.

Due to the surprising discovery that P188 did not provide robust stability to the PCV15 formulation containing conjugates generated by reductive amination in DMSO, additional stabilizers and excipients were screened. PCV15$_{Aq/Non-Aq/ST3-DTFB}$ formulations (with APA in 20 mM L-histidine, pH 5.8, 150 mM NaCl and various stabilizers) were dispensed into syringes and screened using horizontal agitation. The impact of time under constant horizontal rotation was evaluated using visual assessment (Table 2).

Visual assessment of PCV15$_{Aq/Non-Aq/ST3-DTFB}$ formulations indicated no sign of aggregation at higher P188 and PS-20 concentrations (Table 2). However, higher resolution studies to assess subvisible particle size distribution of PCV15$_{Aq/Non-Aq/ST3-DTFB}$ formulations containing P188 (0.05% w/v to 1.0% w/v) or PS-20 (0.005% w/v-0.1% w/v) were conducted using SLS. These formulations were horizontally rotated for up to 24 hours in 1.5 mL HyPak syringes (Becton-Dickinson). D[4,3] values as measured by SLS are shown in FIG. 10A-B. D[4,3] results show higher concentrations of PS-20 significantly improved the physico-chemical stability of the formulation while P188 at all concentrations was not effective.

Example 10: Infant Rhesus Monkey (IRM) Immunogenicity Study Using ST3-DTFB Conjugate Formulated in PCV15

DTFB prepared as described in Example 1 (multimodal cation exchange chromatography) was used to prepare ST3-DTFB conjugate as described in Example 3. PCV15 formulations were prepared as in Example 7. IRMs (Infant Rhesus Monkeys, n=8/group) were intramuscularly (Arms 1-4) immunized with 100 μL vaccine, as described in the Table 3 below on days 0, 28 and 56. Sera were collected prior to study start (pre) and on days 14, 28, 42, 56 and 70. IRMs were observed twice daily by trained animal care staff for any signs of illness or distress. The vaccine formulations in IRMs were deemed to be safe and well tolerated, as no vaccine-related adverse events were noted.

TABLE 2

Visual observation of PCV15$_{Aq/Non-Aq/ST3-DTFB}$ formulations containing 64 μg PnPs/mL and 250 μg/mL APA without surfactant, with P188, with PS-80 or with PS-20 after 1 hour of stirring and up to 24 hours of horizontal rotation in syringes. Fanning refers to the deposition of drug product formulation on the surface of the container closure system (e.g. syringe or vial) and is indicative of surface precipitation of the formulation

| PCV15 Formulation | No Rotation | 1 hr Rotation | 3 hr Rotation | 6 hr Rotation | 8.5 hr Rotation | 24 hr Rotation |
|---|---|---|---|---|---|---|
| No surfactant | No aggregation | Slight Fanning | Fanning | Fanning | Fanning | Particulates |
| 0.05% w/v P188 | No aggregation | Fanning | Fanning | Fanning | Not tested due to fanning at earlier time points | |
| 0.1% w/v P188 | No aggregation | Small fanning | Small fanning | Small fanning | | |
| 0.5% w/v P188 | No aggregation | No aggregation | No aggregation | No aggregation | No aggregation | No aggregation |
| 0.7% w/v P188 | No aggregation | No aggregation | No aggregation | No aggregation | No aggregation | No aggregation |
| 1.0% w/v P188 | No aggregation | No aggregation | No aggregation | No aggregation | No aggregation | No aggregation |
| 0.005% w/v PS-80 | No aggregation | Fanning | Fanning | Fanning | Not tested due to fanning or particulates at earlier time points | |
| 0.01% w/v PS-80 | No aggregation | Fanning | Fanning | Fanning | | |
| 0.05% w/v PS-80 | No aggregation | Fanning | Fanning | Fanning | | |
| 0.005% w/v PS-20 | No aggregation | Fanning | Fanning and small particulates | Fanning and large particulates | | |
| 0.01% w/v PS-20 | No aggregation | Fanning | Fanning | Fanning and large particulates | | |
| 0.05% w/v PS-20 | No aggregation | No aggregation | No aggregation | Small fanning | Small fanning | Particulates |
| 0.07% w/v PS-20 | No aggregation | No aggregation | No aggregation | No aggregation | No aggregation | No aggregation |
| 0.1% w/v PS-20 | No aggregation | No aggregation | No aggregation | No aggregation | No aggregation | No aggregation |

TABLE 3

Infant Rhesus Monkey study formulations

| Arm | Formulation | PnPs dose (μg) | Conjugation process | Protein carrier for serotype 3 |
|---|---|---|---|---|
| 1 | PCV15$_{Aq}$ in 20 mM L-histidine, 150 mM NaCl, 0.2% w/v P188, 250 μg/mL APA | 0.8 μg for 6B, 0.4 μg for all other serotypes | All PnPs serotypes conjugated to protein carrier in aqueous solution | CRM$_{197}$ |
| 2 | PCV15$_{Aq/Non-Aq}$ in 20 mM L-histidine, 150 mM NaCl, 0.2% w/v P188, 250 μg/mL APA | | Serotypes 6A, 6B, 7F, 19A, 19F, 23F conjugated to protein carrier in DMSO; other serotypes conjugated to protein carrier in aqueous solution | |
| 3 | PCV15$_{Aq/Non-Aq/ST3-DTFB}$ in 20 mM L-histidine, 150 mM NaCl, 0.2% w/v P188, 250 μg/mL APA | | | DTFB |
| 4 | PCV15$_{Aq/Non-Aq/ST3-DTFB}$ in 20 mM L-histidine, 150 mM NaCl, 0.1% w/v PS-20, 250 ug/mL APA | | | |

Mouse studies described in Example 6 were completed using monovalent conjugates with a single PnPs serotype 3 WHO ELISA completed to evaluate IgG responses. To assess serotype-specific IgG responses in a 15-valent vaccine, a multiplexed electrochemiluminescence (ECL) assay was developed for use with rhesus monkey serum based on the human assay described by Marchese et al. using MSD technology (MSD is a trademark of MesoScale Discovery, a division of MesoScale Diagnostics, LLC., Gaithersburg, Md., U.S.A.) which utilizes a SULFO-TAG™ label that emits light upon electrochemical stimulation. Human antibody reagents and standards were used when testing the infant monkey samples. The infant rhesus monkey results were expressed as geometric mean concentrations read from a standard curve using the serotype-specific IgG concentrations assigned to the human reference standard (007sp).

Serotype 3 post-dose 3 (PD3) IgG responses (FIG. 11) did not show any statistical differences among immunized groups. Functional antibody, evaluated in OPA assays using S. pneumoniae serotype 3 (FIG. 12), did not show any show any statistical differences among immunized groups.

Example 11: Optimization of PCV15 Formulation

Since the results were very similar between the two formulations at different concentrations of conjugates and APA listed in Example 7, only results for PCV15 formulation containing lower concentrations of conjugates and APA were shown in this example, unless otherwise specified.

A recirculation line is used in the PCV15 formulation process to supply vaccine drug product to the syringe and vial filling machine. Recirculation during routine filling imparts additional shear and stress on biotherapeutic drug products and is therefore an important processing step to evaluate. Studies were conducted to evaluate the impact of recirculation on the PCV15$_{Aq/Non-Aq/ST3-DTFB}$ formulations (in 20 mM L-histidine, pH 5.8, 150 mM NaCl with 64 μg/mL total Polysaccharide and 250 μg/mL APA) containing 0.2% w/v P188 and 0.1% w/v PS-20. The formulations were recirculated for 24 hours from a feed container through tubing at a flow rate of 180 mL/min using a peristaltic pump. The feed container was continuously mixed using a magnetic stir bar, and samples were periodically taken for visual observation. Formulations containing P188 showed the appearance of clumping or visual aggregation (Table 4), while formulations containing PS-20 showed no signs of visible aggregation.

TABLE 4

Visual assessment of PCV15 formulations containing 0.2% w/v P188 or 0.1% w/v PS-20 during 24 hours of continuous mixing and recirculation

| PCV15 Formulation | Recirculation time | | | | | | | |
|---|---|---|---|---|---|---|---|---|
| | 0 hours | 0.5 hours | 1 hour | 3 hours | 6 hours | 8 hours | 12 hours | 24 hours |
| PCV15$_{Aq/Non-Aq/ST3-DTFB}$ with 0.2% w/v P188 | No | No | No | No | No | No | No | Yes |
| PCV15$_{Aq/Non-Aq/ST3-DTFB}$ with 0.1% w/v PS-20 | No | No | No | No | No | No | No | No |

No = No aggregation;
Yes = Aggregation observed in recirculation bottle

Additional recirculation studies were conducted using PCV15$_{Aq/Non-Aq}$ and PCV15$_{Aq/Non-Aq/ST3-DTFB}$ formulations with up to 500 μg/mL (w/v Al$^{+3}$) APA, and with P188 or PS-20. After 24 hours of recirculation with constant mixing, formulations were dispensed into syringes and horizontally agitated for up to 24 hours. The formulations were inspected, and a summary of the visual assessment for the syringes are shown in Table 5. These results indicate that PS-20 provides a robust solution to physical instability or aggregation that may occur during routine manufacturing and shipping and handling. P188 was unable to provide an adequate stability profile for the PCV15$_{Aq/Non-Aq/ST3-DTFB}$ formulation despite its success in stabilizing PCV15$_{Aq}$ formulations (FIGS. 7-9).

TABLE 5

Visual assessment of PCV15 formulations with 0.1% w/v PS-20 or 0.2% w/v P188 after 24 hours of mixing and recirculation and up to 24 hours of horizontal rotation in 1.5 mL HyPak syringes

| PCV15 Formulation | Horizontal rotation time after 24 hours of recirculation | | | | | |
|---|---|---|---|---|---|---|
| | 0 hours | 1 hour | 3 Hours | 6 hours | 10 hours | 24 Hours |
| PCV15$_{Aq/Non-Aq/ST3-DTFB}$ with 0.2% w/v P188 | Small aggregates | Small aggregates | Small aggregates | Large aggregates | Extra large aggregates | Extra large aggregates completely precipitated |
| PCV15$_{Aq/Non-Aq/ST3-DTFB}$ with 0.1% w/v PS-20 | No aggregation | No aggregation | No aggregation | No aggregation | No aggregation | No aggregation |
| PCV15$_{Aq/Non-Aq}$ with 0.1% w/v PS-20 | No aggregation | No aggregation | No aggregation | No aggregation | No aggregation | No aggregation |

As shown in FIG. 10 and Tables 4-5, P188 alone provided minimal benefit in preventing aggregation of suspension-based PCV15 formulations composed of conjugates generated using reductive amination in DMSO and/or ST3-DTFB conjugate. Additional mixing and horizontal rotation studies were conducted with formulations containing 0.2% w/v P188 and PEG400 (PEG) or Propylene Glycol (PG) stabilizers. PCV15$_{Aq/Non-Aq/ST3-DTFB}$ formulations were prepared at 500 mL scale as described in Example 7. PEG400 or PG was added to the APA, and conjugates were then added. The final concentration of PEG400 or PG was between 0% w/v to 15% w/v in the formulation containing 64 µg PnPs/mL, 250 µg/mL APA, and 0.2% w/v P188. Formuations were mixed continuously for 1 hour with a magnetic stir bar and were dispensed into syringes. Syringes were horizontally agitated for up to 24 hours. The formulations were periodically sampled for visual assessment and for particle size distribution measurements by SLS. Results from visual assessment of syringes are shown in Tables 6 and 7. Particle size distribution results are shown in FIGS. 13A-C. When added alone, P188 did not control aggregation in the formulation. Surprisingly, PEG400 or PG provided adequate stability when combined with P188.

TABLE 6

Visual assessment of PCV15 formulations with 0.2% w/v P188 and various PEG$_{400}$ concentrations after 1 hour of mixing and up to 24 hours of horizontal rotation in 1.5 mL HyPak syringes

| PCV15$_{Aq/Non-Aq/ST3-DTFB}$ with 0.2% w/v P188 | Horizontal rotation time after 1 hour of mixing | | | | |
|---|---|---|---|---|---|
| | 0 Hours | 3 hour | 6 hours | 18 hours | 24 Hours |
| with 0% PEG$_{400}$ | No aggregation | No aggregation | Small aggregates | Large aggregates; fanning | Large aggregates; considerable fanning |
| with 6% PEG$_{400}$ | No aggregation | No aggregation | No aggregation | Slight fanning ring | Small aggregates; Slight fanning |
| with 8% PEG$_{400}$ | No aggregation | No aggregation | No aggregation | No aggregation | Slight fanning ring |
| with 10% PEG$_{400}$ | No aggregation | No aggregation | No aggregation | No aggregation | No aggregation |
| with 12% PEG$_{400}$ | No aggregation | No aggregation | No aggregation | No aggregation | No aggregation |
| with 15% PEG$_{400}$ | No aggregation | No aggregation | No aggregation | No aggregation | No aggregation |

TABLE 7

Visual assessment of PCV15 formulations with 0.2% w/v P188 and various PG concentrations after 1 hour of mixing and up to 24 hours of horizontal rotation in 1.5 mL HyPak syringes

| PCV15$_{Aq/Non-Aq/ST3-DTFB}$ with 0.2% w/v P188 | Horizontal rotation time after 1 hour of mixing | | | | |
|---|---|---|---|---|---|
| | 0 Hours | 3 hour | 6 hours | 18 hours | 24 Hours |
| with 0% PG | No aggregation | No aggregation | Small aggregates | Large aggregates; slight fanning | Large aggregates; fanning |
| with 8% PG | No aggregation | No aggregation | No aggregation | No aggregation | Small aggregates |
| with 10% PG | No aggregation | No aggregation | No aggregation | No aggregation | No aggregation |
| with 15% PG | No aggregation | No aggregation | No aggregation | No aggregation | No aggregation |

Example 12: Immunogenicity of Stabilizing Formulations of Pneumococcal Conjugate Vaccine The impact of PCV15 containing formulations that had been optimized to control manufacturing and shipping induced instability on Infant Rhesus Monkey immunogenicity was assessed. Eight animals per group received an intramuscular injection with 0.1 mL of PCV15$_{Aq/Non-Aq/ST3-DTFB}$ formulation containing 64 µg PnPs/mL, 20 mM L-histidine, pH 5.8, 150 mM sodium chloride, 250 µg/mL APA, and either 0.2% w/v P188, 15% w/v PG or 0.1% w/v PS-20 as described in Example 11. Injections were administered at T=0 (Dose 1), 1 month (Dose 2) and 2 months (Dose 3) of age. Serum was collected prior to Dose 1 and 2 weeks post dose 1, 2, and 3. The serum IgG levels from the pre-immune, post dose-1, post dose-2, and post dose-3 serum samples were determined as described above in Example 10. The results shown in FIG. 14 indicate that PCV15 formulations with either PS-20 or a combination of P188 and PG were immunogenic.

What is claimed is:

1. An immunogenic composition comprising a *Streptococcus pneumoniae* serotype 3 polysaccharide-carrier protein conjugate, wherein the carrier protein is diphtheria toxin fragment B (DTFB) or a variant thereof, wherein the variant has at least 90%, 95% or 99% sequence homology to the DTFB carrier protein, including deletions, substitutions and additions; and further comprising additional *Streptococcus pneumoniae* polysaccharide-carrier protein conjugates, wherein the carrier protein is not a DTFB carrier protein or a variant thereof, wherein the variant has at least 90%, 95% or 99% sequence homology to the DTFB carrier protein, including deletions, substitutions and additions.

2. The immunogenic composition of claim 1 wherein the carrier protein of the *Streptococcus pneumoniae* serotype 3 polysaccharide-carrier protein conjugate is DTFB.

3. The immunogenic composition of claim 1, wherein the additional *Streptococcus pneumoniae* polysaccharide-carrier protein conjugates consist of polysaccharides selected from one or more of serotypes 1, 2, 4, 5, 6A, 6B, 6C, 6D, 7B, 7C, 7F, 8, 9N, 9V, 10A, 11A, 12F, 14, 15A, 15B, 15C, 16F, 17F, 18C, 19A, 19F, 20, 21, 22A, 22F, 23A, 23B, 23F, 24F, 27, 28A, 31, 33F, 34, 35A, 35B, 35F, and 38.

4. The immunogenic composition of claim 1 wherein the carrier protein of the additional *Streptococcus pneumoniae* polysaccharide-carrier protein conjugate is CRM$_{197}$.

5. The immunogenic composition of claim 1, wherein the additional *Streptococcus pneumoniae* polysaccharide-carrier protein conjugates consist of polysaccharides selected from serotypes 1, 4, 5, 6A, 6B, 7F, 9V, 14, 18C, 19A, 19F, 22F, 23F, and 33F and the carrier protein is CRM$_{197}$.

6. The immunogenic composition of claim 5, further comprising an adjuvant.

7. The immunogenic composition of claim 6, wherein the adjuvant is an aluminum-based adjuvant.

8. The immunogenic composition of claim 7, wherein the adjuvant is selected from the group consisting of aluminum phosphate, aluminum sulfate and aluminum hydroxide.

9. The immunogenic composition of claim 8, wherein the adjuvant is aluminum phosphate.

10. The immunogenic composition of claim 9, wherein the immunogenic composition is formulated to contain: 4 µg/mL of each polysaccharide, except for 6B which contains 8 µg/mL of polysaccharide; about 64 µg/mL CRM$_{197}$ carrier protein; about 4 µg/mL of DTFB carrier protein; 0.25 mg/mL aluminum phosphate adjuvant; 150 mM sodium chloride; 20 mM L-histidine buffer; and 0.2% w/v polysorbate-20 (PS-20).

* * * * *